US012582478B2

(12) United States Patent
Yoon et al.

(10) Patent No.: US 12,582,478 B2
(45) Date of Patent: Mar. 24, 2026

(54) SYSTEMS AND METHODS FOR INTEGRATING INTRAOPERATIVE IMAGE DATA WITH MINIMALLY INVASIVE MEDICAL TECHNIQUES

(71) Applicant: INTUITIVE SURGICAL OPERATIONS, INC., Sunnyvale, CA (US)

(72) Inventors: Sungwon Yoon, Palo Alto, CA (US); Hui Zhang, San Jose, CA (US); Troy K. Adebar, San Jose, CA (US); Cristian Bianchi, Capannori (IT); Carlo Camporesi, Alameda, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 348 days.

(21) Appl. No.: 18/259,854

(22) PCT Filed: Dec. 28, 2021

(86) PCT No.: PCT/US2021/065322
§ 371 (c)(1),
(2) Date: Jun. 29, 2023

(87) PCT Pub. No.: WO2022/146992
PCT Pub. Date: Jul. 7, 2022

(65) Prior Publication Data
US 2024/0099776 A1 Mar. 28, 2024

Related U.S. Application Data

(60) Provisional application No. 63/132,258, filed on Dec. 30, 2020.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/361* (2016.02); *A61B 90/37* (2016.02);
(Continued)

(58) Field of Classification Search
CPC ....... A61B 34/10; A61B 34/20; A61B 90/361; A61B 90/37; G06T 7/12; G06T 7/30; G16H 30/20; G06V 10/25
See application file for complete search history.

(56) References Cited

U.S. PATENT DOCUMENTS 11,172,989 B2 * 11/2021 Weingarten ........... G06T 19/003
11,253,325 B2 * 2/2022 Birenbaum ............ A61B 6/466
(Continued)

FOREIGN PATENT DOCUMENTS

EP 2666430 A1 11/2013
WO WO-03045222 A2 6/2003
(Continued)

OTHER PUBLICATIONS

International Search Report and Written Opinion for Application No. PCT/US2021/065322, mailed Apr. 8, 2022, 16 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
(Continued)

*Primary Examiner* — Mohammed H Zuberi
(74) *Attorney, Agent, or Firm* — Haynes & Boone, LLP.

(57) ABSTRACT

A system may comprise a processor and a memory having computer readable instructions stored thereon. The computer readable instructions, when executed by the processor, cause the system to record shape data for an instrument during an image capture period of an imaging system and receive image data from the imaging system corresponding to the image capture period. A portion of the image data
(Continued)

900

902 — RECORD SHAPE DATA DURING AN IMAGE CAPTURE PERIOD

904 — RECEIVE IMAGING DATA CORRESPONDING TO THE IMAGE CAPTURE PERIOD

906 — IDENTIFY TARGET IN THE IMAGE DATA

908 — SEGMENT PORTION OF THE IMAGING DATA CORRESPONDING TO THE INSTRUMENT

910 — REGISTER IMAGE DATA TO THE SHAPE DATA

912 — UPDATE LOCATION OF THE TARGET FROM A PRE-OPERATIVE LOCATION TO AN INTRA-OPERATIVE LOCATION corresponds to the instrument. The computer readable instructions further cause the system to identify a target in the image data, segment the portion of the image data, register the image data to the shape data by comparing the shape data to the portion of the image data corresponding to the instrument, and update a location of the target from a pre-operative location to an intra-operative location based upon the image data.

20 Claims, 13 Drawing Sheets

(51) Int. Cl.

| | | |
|---|---|---|
| *A61B 90/00* | (2016.01) | |
| *G06T 7/12* | (2017.01) | |
| *G06T 7/30* | (2017.01) | |
| *G06V 10/25* | (2022.01) | |
| *G16H 30/20* | (2018.01) | |

(52) U.S. Cl.
CPC ................. *G06T 7/12* (2017.01); *G06T 7/30* (2017.01); *G06V 10/25* (2022.01); *G16H 30/20* (2018.01); *A61B 2034/2061* (2016.02); *G06V 2201/07* (2022.01)

(56) References Cited

U.S. PATENT DOCUMENTS

| | | | | |
|---|---|---|---|---|
| 11,269,173 | B2 * | 3/2022 | Komp | A61B 34/30 |
| 11,341,692 | B2 * | 5/2022 | Weingarten | G06T 19/003 |
| 11,341,720 | B2 * | 5/2022 | Alexandroni | G06T 5/20 |
| 11,357,593 | B2 * | 6/2022 | Komp | A61B 1/0005 |
| 11,364,004 | B2 * | 6/2022 | Barak | A61B 6/487 |
| 11,378,378 | B2 * | 7/2022 | Fujihara | G01B 5/008 |
| 11,380,060 | B2 * | 7/2022 | Barasofsky | G06T 7/162 |
| 11,589,929 | B2 | 2/2023 | Ekin | |
| 2007/0031018 | A1 * | 2/2007 | Camus | A61B 6/481 |
| | | | | 382/130 |
| 2019/0313986 | A1 * | 10/2019 | Do | A61B 6/12 |
| 2019/0320878 | A1 * | 10/2019 | Duindam | G06T 7/30 |

FOREIGN PATENT DOCUMENTS

| | | | |
|---|---|---|---|
| WO | WO-2018129532 | A1 | 7/2018 |
| WO | WO-2018195216 | A1 | 10/2018 |

OTHER PUBLICATIONS

International Preliminary Report on Patentability for Application No. PCT/US2021/065322 mailed Jul. 13, 2023, 10 pages.

* cited by examiner

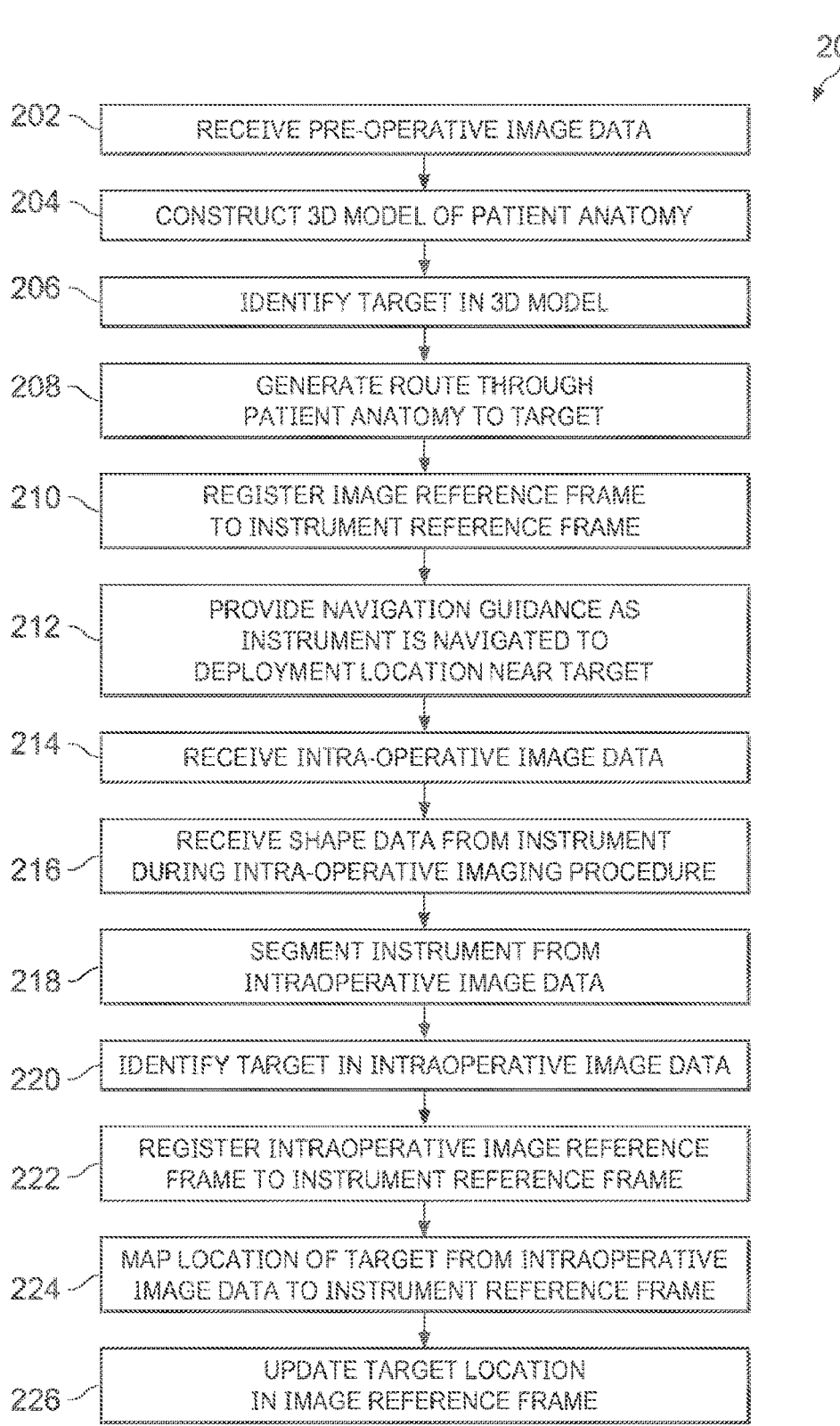

*200*

202 — RECEIVE PRE-OPERATIVE IMAGE DATA

204 — CONSTRUCT 3D MODEL OF PATIENT ANATOMY

206 — IDENTIFY TARGET IN 3D MODEL

208 — GENERATE ROUTE THROUGH PATIENT ANATOMY TO TARGET

210 — REGISTER IMAGE REFERENCE FRAME TO INSTRUMENT REFERENCE FRAME

212 — PROVIDE NAVIGATION GUIDANCE AS INSTRUMENT IS NAVIGATED TO DEPLOYMENT LOCATION NEAR TARGET

214 — RECEIVE INTRA-OPERATIVE IMAGE DATA

216 — RECEIVE SHAPE DATA FROM INSTRUMENT DURING INTRA-OPERATIVE IMAGING PROCEDURE

218 — SEGMENT INSTRUMENT FROM INTRAOPERATIVE IMAGE DATA

220 — IDENTIFY TARGET IN INTRAOPERATIVE IMAGE DATA

222 — REGISTER INTRAOPERATIVE IMAGE REFERENCE FRAME TO INSTRUMENT REFERENCE FRAME

224 — MAP LOCATION OF TARGET FROM INTRAOPERATIVE IMAGE DATA TO INSTRUMENT REFERENCE FRAME

226 — UPDATE TARGET LOCATION IN IMAGE REFERENCE FRAME

FIG. 2

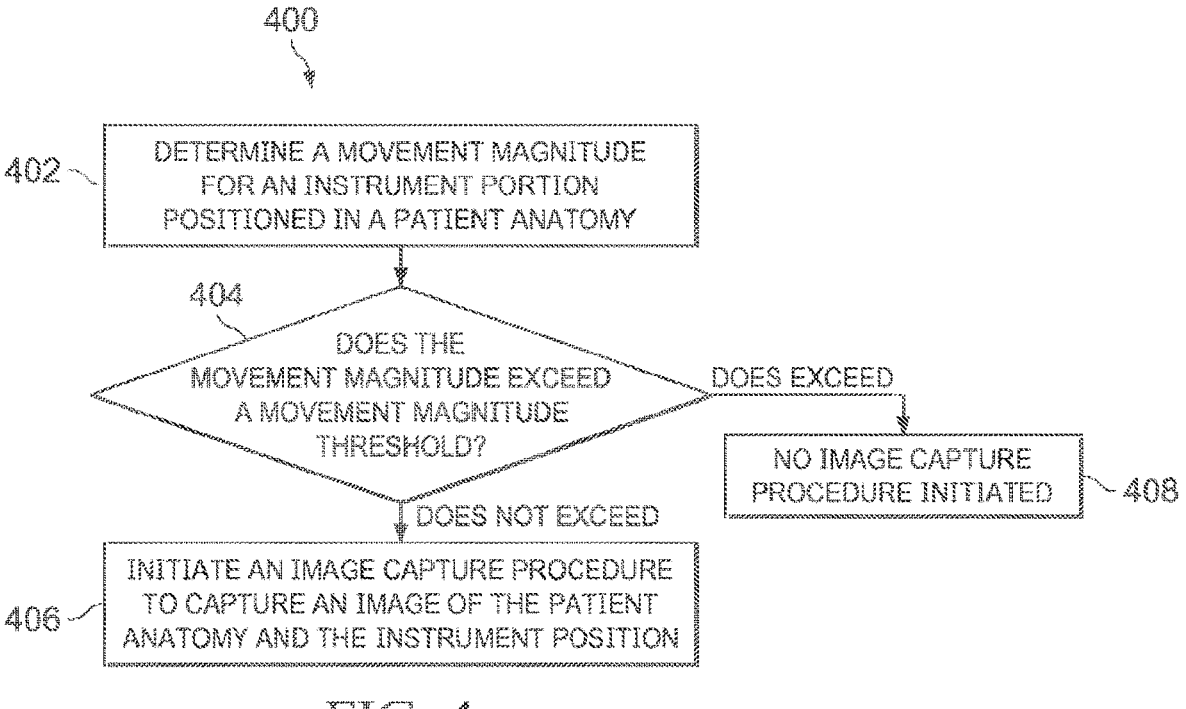

400

402 — DETERMINE A MOVEMENT MAGNITUDE
FOR AN INSTRUMENT PORTION
POSITIONED IN A PATIENT ANATOMY

404 — DOES THE
MOVEMENT MAGNITUDE EXCEED
A MOVEMENT MAGNITUDE
THRESHOLD?

DOES EXCEED

NO IMAGE CAPTURE
PROCEDURE INITIATED — 408

DOES NOT EXCEED

406 — INITIATE AN IMAGE CAPTURE PROCEDURE
TO CAPTURE AN IMAGE OF THE PATIENT
ANATOMY AND THE INSTRUMENT POSITION

FIG. 4

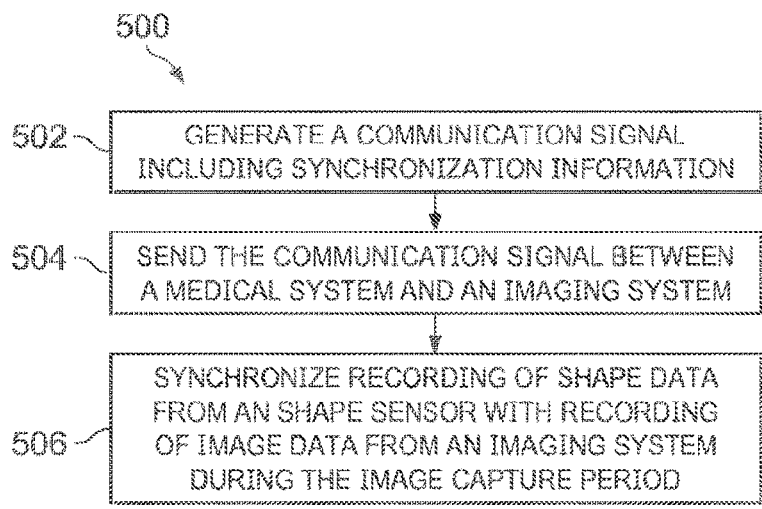

500

502 — GENERATE A COMMUNICATION SIGNAL
INCLUDING SYNCHRONIZATION INFORMATION

504 — SEND THE COMMUNICATION SIGNAL BETWEEN
A MEDICAL SYSTEM AND AN IMAGING SYSTEM

506 — SYNCHRONIZE RECORDING OF SHAPE DATA
FROM AN SHAPE SENSOR WITH RECORDING
OF IMAGE DATA FROM AN IMAGING SYSTEM
DURING THE IMAGE CAPTURE PERIOD

| 902 | RECORD SHAPE DATA DURING AN IMAGE CAPTURE PERIOD |
| 904 | RECEIVE IMAGING DATA CORRESPONDING TO THE IMAGE CAPTURE PERIOD |
| 906 | IDENTIFY TARGET IN THE IMAGE DATA |
| 908 | SEGMENT PORTION OF THE IMAGING DATA CORRESPONDING TO THE INSTRUMENT |
| 910 | REGISTER IMAGE DATA TO THE SHAPE DATA |
| 912 | UPDATE LOCATION OF THE TARGET FROM A PRE-OPERATIVE LOCATION TO AN INTRA-OPERATIVE LOCATION |

1000

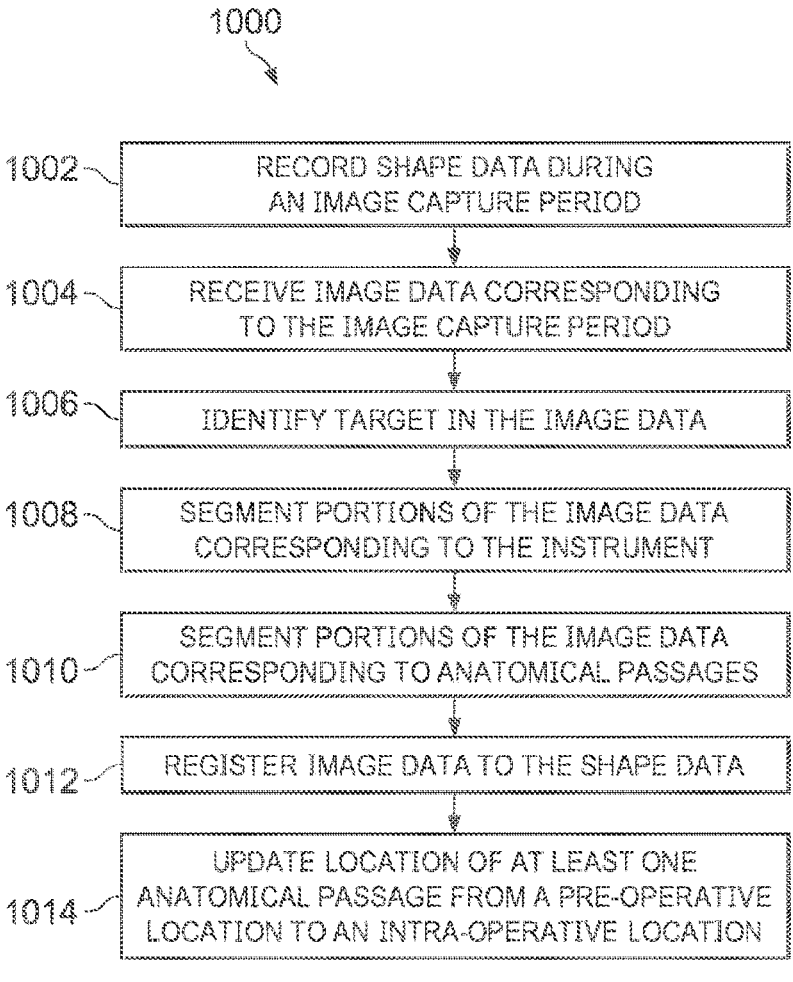

| | |
|---|---|
| 1002 | RECORD SHAPE DATA DURING AN IMAGE CAPTURE PERIOD |
| 1004 | RECEIVE IMAGE DATA CORRESPONDING TO THE IMAGE CAPTURE PERIOD |
| 1006 | IDENTIFY TARGET IN THE IMAGE DATA |
| 1008 | SEGMENT PORTIONS OF THE IMAGE DATA CORRESPONDING TO THE INSTRUMENT |
| 1010 | SEGMENT PORTIONS OF THE IMAGE DATA CORRESPONDING TO ANATOMICAL PASSAGES |
| 1012 | REGISTER IMAGE DATA TO THE SHAPE DATA |
| 1014 | UPDATE LOCATION OF AT LEAST ONE ANATOMICAL PASSAGE FROM A PRE-OPERATIVE LOCATION TO AN INTRA-OPERATIVE LOCATION |

FIG. 10

SYSTEMS AND METHODS FOR INTEGRATING INTRAOPERATIVE IMAGE DATA WITH MINIMALLY INVASIVE MEDICAL TECHNIQUES

CROSS-REFERENCE TO RELATED APPLICATIONS

This application is the national phase of PCT/US2021/065321 filed on Dec. 28, 2021 which claims the benefit of and priority to U.S. Provisional Application 63/132,258, filed Dec. 30, 2020, both of which are incorporated by reference herein in their entirety.

FIELD

The present disclosure is directed to systems and methods for planning and performing an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways, obtained pre-operatively and/or intra-operatively. Improved systems and methods are needed to enhance procedure workflow by coordinating medical tools and images of the anatomic passageways.

SUMMARY

Consistent with some embodiments, a system may comprise a processor and a memory having computer readable instructions stored thereon. The computer readable instructions, when executed by the processor, may cause the system to perform a method including recording shape data for an instrument during an image capture period of an imaging system and receiving image data from the imaging system corresponding to the image capture period. A portion of the image data may correspond to the instrument. The method performed by the system may further include identifying a target in the image data, segmenting the portion of the image data corresponding to the instrument, registering the image data to the shape data by comparing the shape data to the portion of the image data corresponding to the instrument and updating a location of the target from a pre-operative location to an intra-operative location based upon the image data.

Consistent with some embodiments, a method that may comprise recording shape data for an instrument during an image capture period of an imaging system and receiving image data from the imaging system corresponding to the image capture period. A portion of the image data may correspond to the instrument. The method may further include identifying a target in the image data, segmenting the portion of the image data, registering the image data to the shape data by comparing the shape data to the portion of the image data corresponding to the instrument, and updating a location of the target from a pre-operative location to an intra-operative location based upon the image data.

Consistent with some embodiments, a system may comprise a processor and a memory having computer readable instructions stored thereon. The computer readable instructions, when executed by the processor, may cause the system to perform recording shape data for an instrument disposed in anatomic passages of a patient during an image capture period of an imaging system and receiving image data from the imaging system corresponding to the image capture period. A portion of the image data may correspond to the instrument. The computer readable instructions, when executed by the processor, may further cause the system to perform identifying a target in the image data, segmenting the portion of the image data corresponding to the instrument, segmenting portions of the image data corresponding to the anatomic passages, registering the image data to the shape data by comparing the shape data to the portion of the image data corresponding to the instrument, and updating a location of at least one of the anatomic passages from a pre-operative location to an intra-operative location based upon the image data.

Other embodiments include corresponding computer systems, apparatus, and computer programs recorded on one or more computer storage devices, each configured to perform the actions of the methods.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2 illustrates a method for updating a location of a target in an anatomic model.

FIG. 4 illustrates a method for evaluating anatomic motion to determine whether an intra-operative imaging procedure should be performed.

FIG. 5 illustrates a method for synchronizing a robot-assisted medical system with an imaging system during an image capture period of the imaging system.

FIG. 10 illustrates a method of registering image data to shape data from an instrument to update a location of an anatomic structure in a model.

Figure 1:
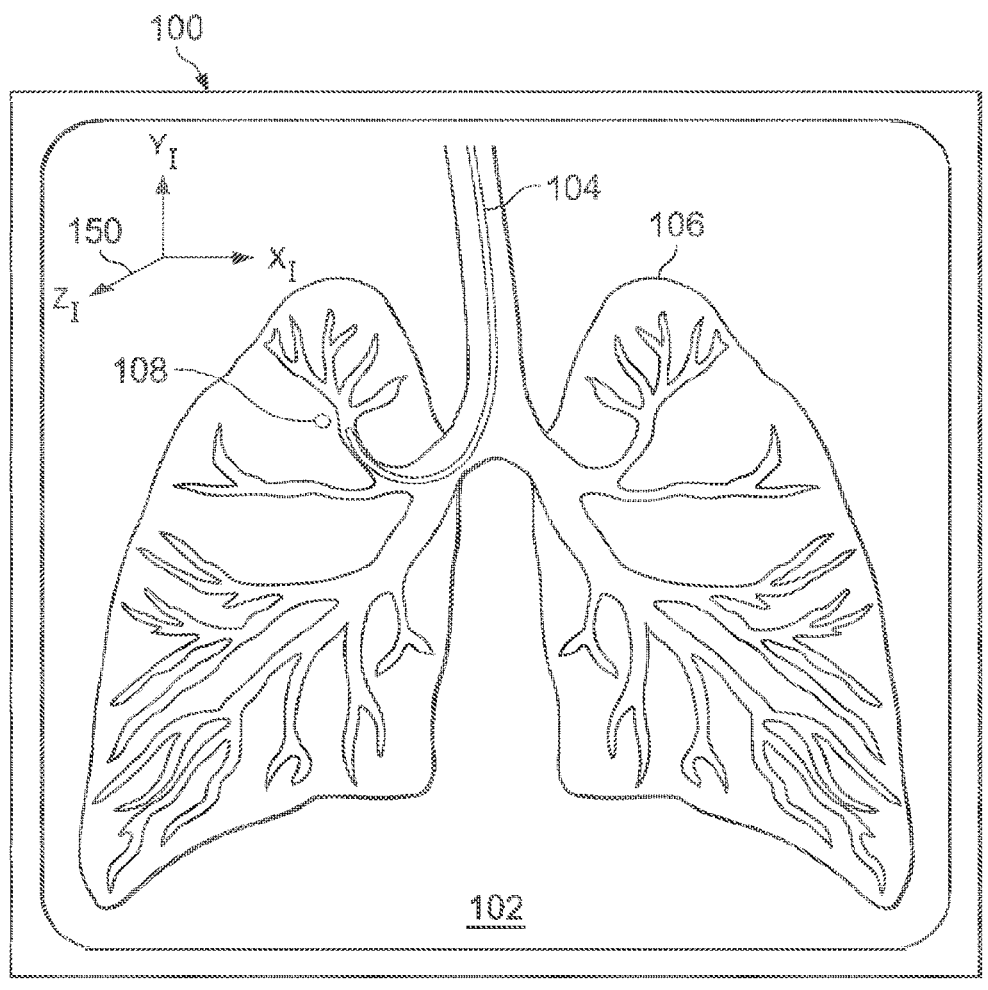
FIG. 1 illustrates a display system displaying an image of a medical instrument registered to an anatomic model.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The techniques disclosed in this document may be used to enhance the workflow processes of minimally invasive procedures using intra-operative imaging, such as cone beam computerized tomography (CT) imaging. In some examples, instrument data may be analyzed prior to initiating an intra-operative imaging procedure to ensure data quality provided by the images. In some examples, the image data produced by the intra-operative imaging may be utilized to refine locations of an instrument, an anatomic structure, or a target in a model constructed from pre-operative imaging.

With reference to FIG. 1, an image-guided surgical procedure, which may be robot-assisted or otherwise teleoperated, may be conducted in which a display system 100 may display a virtual navigational image 102, having an image reference frame $(X_I, Y_I, Z_I)$ 150 in which a medical instrument 104 is registered (i.e., dynamically referenced) with an anatomic model 106 of a patient derived from pre-operative image data obtained, for example, from a CT scan. The anatomic model 106 may include a target 108, such as a lesion or nodule of interest, which the procedure is intended to address (e.g., biopsy, treat, view, etc.). In some embodiments, the virtual navigational image 102 may present a physician with a virtual image of the internal surgical site from a viewpoint of medical instrument 104, for example, from a distal tip of medical instrument 104. In some embodiments, the display system 100 may present a real-time view from the distal tip of medical instrument 104, for example, when the medical instrument 104 comprises an endoscope. In some embodiments, the medical instrument 104 may be manipulated by a robot-assisted manipulator controlled by a control system, or processing system, which includes one or more processors. An example of a robot-assisted medical system will be described further at FIG. 12A.

Generating the virtual navigational image 102 involves the registration of the image reference frame $(X_I, Y_I, Z_I)$ 150 to a surgical reference frame $(X_S, Y_S, Z_S)$ of the anatomy and/or medical instrument reference frame $(X_M, Y_M, Z_M)$ of the medical instrument 104. This registration may rotate, translate, or otherwise manipulate by rigid or non-rigid transforms points associated with the segmented instrument shape from the image data and/or points associated with the shape data from a shape sensor disposed along a length of the medical instrument 104. This registration between the image and instrument reference frames may be achieved, for example, by using a point-based iterative closest point (ICP) technique as described in U.S. Pat. App. Pub. Nos. 2018/0240237 and 2018/0235709, incorporated herein by reference in their entireties, or another point cloud registration technique.

FIG. 2 illustrates an example of a method or workflow 200 for performing a minimally invasive procedure in accordance with some aspects of the present disclosure. At a process 202, pre-operative image data is received at a control system. For example, a CT scan of the patient's anatomy may be performed with a conventional fan beam CT scanner and the CT image data may be received by a control system. Alternatively, pre-operative image data may be received from other types of imaging systems including magnetic resonance imaging systems, fluoroscopy systems, or any other suitable method for obtaining dimensions of anatomic structures. At process 204, a three-dimensional (3D) model of the anatomic structures (e.g., anatomic model 106 of FIG. 1) may be constructed from the pre-operative image data by a control system. At process 206, a target may be identified in the 3D model or the pre-operative image data from which it was constructed. For example, the target 108 of FIG. 1 may be identified in the anatomic model 106 as a region of interest for investigation or treatment. The target may be automatically identified by a control system and confirmed by a user or may be visually identified by the user and manually selected or indicated in the 3D model, for example, through the display system 100. At process 208, a route through anatomic passageways formed in the anatomic structures is generated. The route may be generated automatically by the control system, or the control system may generate the route based on user inputs. The route may indicate a path along which a medical instrument (e.g., medical instrument 104 of FIG. 1) may be navigated into close proximity with the target. In some embodiments, the route may be stored in a control system and incorporated into the images displayed on display system 100.

To provide accurate navigation through the anatomic passageways, a reference frame 150 of the pre-operative image data (and subsequently constructed 3D model) may be registered to a reference frame of the medical instrument at process 210. For example, a shape sensor (e.g., a fiber optic shape sensor or one or more position sensors) disposed along a length of the medical instrument may be used to provide real-time shape data (e.g., information regarding a shape of the instrument and/or a position of one or more points along the length of the instrument). This shape data may be utilized to register the instrument to the 3D model constructed from the pre-operative image data and to track a location of the instrument during use. Upon successful registration, a process 212 may include providing navigation guidance as the instrument is navigated through the anatomic passageways to a deployment location in proximity to the target. Navigation may be performed manually by a user with provided navigation guidance, automatically by a control system, or via a combination of both.

With the instrument positioned at or near the deployment location within the anatomy of the patient (e.g., in close proximity to the target), an intra-operative imaging scan may be performed. At a process 214, intra-operative image data may be received at a control system from an intra-operative imaging system. In some examples, the intra-operative imaging system may be a cone beam CT ("CBCT") scanner than generates intra-operative CT scan image data, although any suitable imaging technique may be used without departing from the embodiments of the present disclosure. As compared to other imaging techniques such as conventional CT or fluoroscopy, CBCT imaging may provide a more rapid scan of a region of the patient's anatomy without delaying the procedure and may also have more portable and compact hardware.

As mentioned above, the intra-operative image data may be received at a control system or other processing platform associated with the instrument. It is also contemplated that in some examples the shape data associated with the instrument may be transferred to the imaging system, or both the shape data and the image data may be transferred to a common platform for processing. In this regard, registration of the shape data of the instrument to the intra-operative image data may be performed by the control system, by the imaging system, or by another platform in operable communication with the intra-operative imaging system and the control system. Typically, the communication of the image data to or from the control system will use a Digital Imaging and Communications in Medicine ("DICOM") standard. The image data may also be received in a maximum intensity projection ("MIP") or pseudo-CT streaming format. In some embodiments, receiving the image data may include receiving one or more timestamps associated with the image data. A first timestamp may indicate the start time of the scan and a second timestamp may additionally indicate a stop time of the scan. Alternatively, a timestamp may be associated with each instance of image data. In order to ensure accurate correlation, a clock of the control system of the instrument may be synchronized with a clock of the imaging system and each instance of shape data may also be associated with a timestamp. In this regard, each timestamped instance of image data may be paired with a correspondingly timestamped instance of shape data.

In order to register the intra-operative imaging scan to the instrument, while the intra-operative imaging scan is performed, at a process 216, shape data from the instrument captured during the intra-operative imaging process 214 may be received. The shape data may be captured for only a brief period of time or may be captured during the whole image capture period of the intra-operative imaging scan. A variety of synchronizing techniques, as discussed in further detail below in relation to FIG. 5, may be used to ensure that only shape data corresponding to the image capture period is used for registration, even though shape data outside the image capture period may also be recorded.

At process 218, the image data from the intra-operative scan, or a portion thereof, may be segmented. In this regard, discrete units of the image data (e.g., pixels or voxels) may be analyzed to assign an intensity value to each unit. Discrete units having the same or similar intensity values may be aggregated to form components. Morphological operations may be utilized to interconnect non-contiguous components having similar intensity values.

In some embodiments, segmenting the image data may comprise selecting components to associate with certain objects. For example, segmenting the image data associated with the instrument may include selecting imaging units or components based upon one or more factors including proximity to the target, the shape data, an approximate registration of the instrument to the patient, and an expected instrument intensity value. An expected instrument intensity value may include a range of values associated with materials from which the instrument is composed. In some embodiments, an algorithm (e.g., Gaussian Mixture Model)

may be used to establish the expected instrument intensity. In some embodiments, segmenting the image data may further comprise utilizing processes established by the control system using deep learning techniques.

Information about the instrument may be used to seed the segmentation process. For example, an instrument (e.g., a steerable catheter) may include a metal spine embedded in a non-metal sheath. In this regard, high contrast in the intra-operative image data associated with the spine may be identified first, and a region around the spine may be searched for the non-metal sheath in pixels or voxels having less contrast. In a similar regard, a high-contrast fiducial marker may be inserted through a working channel of an instrument during intra-operative imaging to improve segmentation of the instrument.

In some instances, segmenting of the instrument may be determined to have produced unsatisfactory results. For example, the segmentation may have resulted in a plurality of non-contiguous components with gaps in between. Alternatively, the segmentation may have resulted in an instrument dimension that is known to be inaccurate. For example, the segmented instrument in the intra-operative image data may appear to have a diameter of 1 mm or 10 mm when it is known that the instrument has a diameter of 5 mm. As another example, it may be determined that one or more relevant portions of the instrument are outside the volume of the intra-operative image data.

As a result of determining the segmentation to be unsatisfactory, the control system may implement a low accuracy mode in which registration of the intra-operative image data to the instrument may proceed with translation movements only (e.g., movement only along the X-, Y-, and/or Z-axes) while preventing rotations. Alternatively, unsatisfactory results of segmentation may result in an instruction or prompt being generated to direct a user to identify the instrument in the image data, for example, by using an input device and the display system to select components associated with the instrument per process 212 above.

At a process 220, the target may be identified in the intra-operative image data. In some embodiments, when the instrument has already been segmented or identified, identifying the target may comprise establishing a region of interest in the image data within a predetermined range of the instrument. The region of interest may then be analyzed to segment the target from the region of interest. In this regard, the search field in which to locate the target may be reduced based upon an assumption that the instrument was previously navigated into close proximity with the target. In some embodiments, identifying the target may include receiving an indication or selection from a user at a user interface. For example, a user may manually select portions of the image data associated with one or more components on the display system to associate with the target. Manual identification of the target may be necessary when automatic identification of the target has produced unsatisfactory results and a user is instructed to manually identify the target in the image data. In some instances, identifying the target in the intra-operative image data may result in registering the pre-operative image data (or 3D model) to the intra-operative image data based upon a pre-operative location of the target and an intra-operative location of the target.

At a process 222, the intra-operative image data may be registered to the shape data by comparing the shape data to the portion of the image data corresponding to the instrument. In some embodiments, this registration may be performed using an iterative closest point algorithm. Optionally, data points may be weighted based upon segmentation confidence or quality to assign more influence to data points which are determined to be more likely to be accurate. Alternatively, registering the intra-operative image data to the shape data may be performed using coherent point drift or an uncertainty metric (e.g., RMS error). In some instances, it may be determined that the registering has produced unsatisfactory results. As a result, the control system may implement the low accuracy mode. Discussion of processes for registering an instrument to image data may be found, for example, in Intl. Pat. Pub. No. WO2021/ 092116 (filed Nov. 5, 2020) (disclosing "Systems and Methods for Registering an Instrument to an Image Using Change in Instrument Position Data") and Intl. Pat. Pub. No. WO2021/092124 (filed Nov. 5, 2020) (disclosing Systems and Methods for Registering an Instrument to an Image Using Point Cloud Data), both of which are incorporated by reference herein in their entireties.

At a process 224, the intra-operative location of the target may be mapped to the instrument reference frame based upon the registration performed in process 222. The intra-operative location of the target may be compared to the pre-operative location of the target. If there is a discrepancy, the target location may be updated to the intra-operative location at a process 226. The updated location of the target may be shown with respect to the 3D model and/or the instrument on the display system to facilitate the procedure.

The method 200 of FIG. 2 may additionally or alternatively include segmenting portions of the image data corresponding to one or more anatomical passageways using similar segmentation techniques as those discussed above. After registering the image data to the shape data, the location of at least one of the anatomical passageways may be updated in the 3D model from a pre-operative location to an intra-operative location based upon the intra-operative image data.

Figure 3:
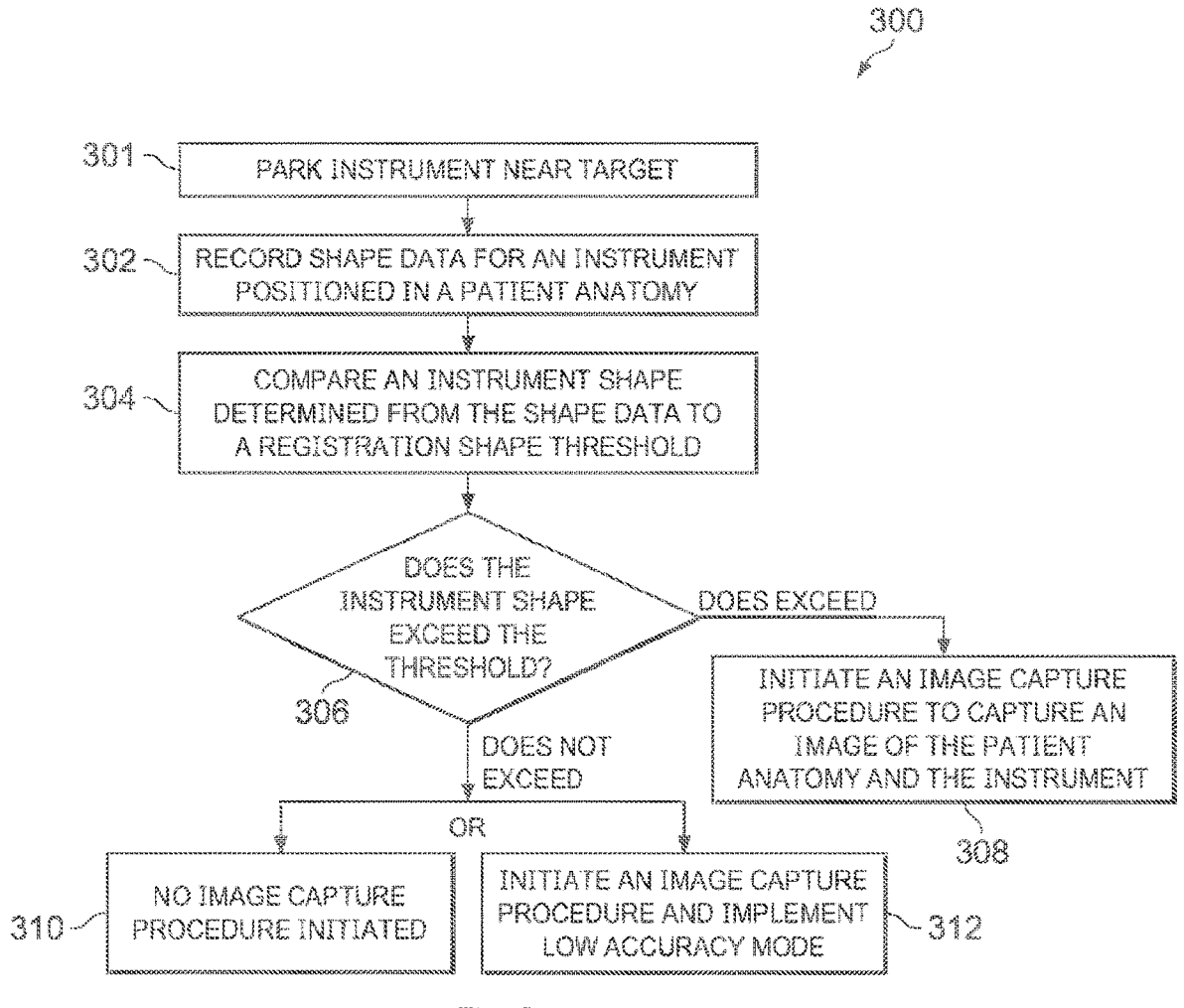
FIG. 3 illustrates a method for evaluating the shape of a medical instrument to determine whether an intra-operative imaging procedure should be performed.

After the instrument is located near a target at process 212 and before the intraoperative imaging is performed at process 214, as described with reference to FIG. 2 above, an evaluation may be performed to determine whether the instrument is arranged in a configuration suitable for use in later registration of the image data to the shape data. FIG. 3 illustrates a method 300 for evaluating the shape of a medical instrument to determine whether an intra-operative imaging procedure should be performed, particularly when administration of the imaging procedure will expose the patient to radiation. As compared to a medical instrument arranged in a straight configuration, shape data from a medical instrument configured with bends in each of the three dimensions may be particularly useful in three-dimensional registration with anatomic image data.

At a process 302, shape data is recorded for an instrument while the instrument is located in the anatomy of a patient. For example, shape data gathered from shape sensor may provide shape information for the instrument, including position and orientation information for a plurality of points along the instrument.

At a process 304, a preliminary shape of the instrument in the recorded instrument shape data is compared to a registration shape threshold. In some embodiments, the registration shape threshold may be a curvature threshold corresponding to a shape that includes a bend in at least one or two of three dimensions in a three-dimensional environment. In some embodiments, the registration shape threshold may be a shape that includes a bend in all three dimensions of the three-dimensional environment. In this example, any viewing plane in the three-dimensional environment will include a curved shape that allows for a full three-dimensional registration.

At a process 306, based on the comparison, a determination is made as to whether the instrument shape determined from the shape data exceeds the registration shape threshold.

At a process 308, if the recorded instrument shape does exceed the registration shape threshold, the shape of the instrument may be considered sufficiently curved to permit image capture. An image capture procedure may be initiated to capture the image data of the patient anatomy and the instrument as described above with reference to process 214.

At a process 310, if the recorded instrument shape does not exceed the registration shape threshold, the shape of the instrument may be considered insufficiently curved or too straight to permit image capture. In some embodiments, instructions may be provided to alert the user that the image capture procedure was not initiation and the reason why it was not initiated. For example, instructions may be provided through text or images displayed on the display system, through audio messages sent to the user, or through other types of communication perceptible by the user. In some embodiments, a textual message such as "Image capture not initiated. Instrument curvature does not meet the bend threshold" may be displayed. In some embodiments, corrective instructions to revise the preliminary shape of the instrument may be further provided. For example, textual instructions may be provided to bend the instrument or otherwise reconfigure the instrument until a bend sufficient to exceed the threshold is reached such that revised configuration is more likely to yield a successful segmentation and/or registration. Additionally or alternatively, a guidance image may be provided to guide the user to bend the instrument to generate a shape as shown in the guidance image.

It should be appreciated that the instrument being too straight to perform registration is only one example of a singularity which may render it difficult or impossible to register the instrument to the image data. For example, the instrument may have a tight bend with a small radius, but the bend may align with a single plane. Similarly, a consistent bend radius along the entire length of the portion of the instrument displayed in image data and portrayed in shape data may render it difficult to differentiate different points along the portion in the image data.

At a process 312, which may be an alternative process to process 310, an image capture procedure may be initiated to capture an image of the patient anatomy and the instrument. However, due to the instrument shape failing to exceed the threshold, the captured image data may be discarded, suppressed, or filtered for use in a registration procedure. In some instances, the low accuracy mode may be implemented to prevent rotational components of registration.

Furthermore, in some embodiments, a determination may be made as to the location of the curvature that exceeds the registration shape threshold. Based on the location of the curvature, a determination may be made as to whether an image of the patient anatomy will include the image of the curvature. If the field of view of the imaging system will not include the curvature, the image capture procedure may not be initiated. The medical instrument may be rearranged until it forms a curvature, within the field of view of the imaging system, that exceeds the curvature threshold. Additionally or alternatively, instructions may be sent to a user to move the imaging system to a different imaging position or imaging orientation to capture an image of the patient anatomy that will include an image of the curvature that exceeds the registration shape threshold.

In some embodiments, prior to initiating an image capture procedure to generate the intra-operative image data of process 214, a determination may be made as to whether the instrument or a portion of the instrument in the proximity of an anatomic target (e.g., a lesion or nodule) is in an area where the anatomic motion (e.g., due to respiratory or cardiac processes) exceeds a threshold for suitable image capture. FIG. 4 illustrates a method 400 for evaluating anatomic motion. Often, anatomic motion can result in intra-operative image data that is too distorted to isolate and segment the medical instrument. Before capturing an intra-operative image of the medical instrument, a magnitude of anatomic motion may be evaluated. If the magnitude of anatomic motion exceeds a threshold amount, any captured images may be distorted and, consequently, may be considered inadequate for use in registration. Instructions may be provided to suspend image capture and/or to move the instrument to a different anatomic area.

At a process 402, a movement magnitude (which may include any measure of movement such as a displacement distance, degree of rotation, velocity, etc.) is determined for an instrument or a portion of an instrument while the instrument is located in the anatomy of a patient. For example, shape data, gathered from a shape sensor, may be recorded for an instrument portion that would be in the field of view of the imaging system during an image capture procedure. The shape data may be recorded during a time period prior to initiation of an image capture procedure when the instrument portion is not subject to commanded motion. A movement magnitude may be determined by evaluating the change in the shape data during the time period.

At a process 404, a determination is made as to whether the movement magnitude exceeds a movement magnitude threshold. The movement magnitude threshold may be predetermined based on the magnitude of motion that will result in an unusable image. The movement magnitude threshold may be a measure of displacement, rotation, velocity, and/or other components of motion.

At a process 406, if the movement magnitude does not exceed the movement magnitude threshold, an image capture procedure may be initiated to capture an image of the patient anatomy and the instrument portion.

At a process 408, if the movement magnitude does exceed the movement magnitude threshold, an image capture procedure may be prevented or suspended. In some embodiments, a user may be instructed to suspend the image capture procedure until movement has subsided (e.g., a breath hold is initiated) or move the instrument to a different anatomic area.

For example, with regard to the method 400, prior to process 214 of FIG. 2, shape data received from a shape sensor of the instrument may be analyzed over a period of time. Using the shape data, it may be determined that a portion of the instrument within the field of view of an imaging system is being displaced with a movement magnitude of 1.5 cm with each breathing cycle of the patient. If a predetermined movement magnitude threshold of 1.0 cm has been established, the control system will determine that the movement magnitude exceeds the movement magnitude threshold. In response, a user may be alerted so that corrective action may be taken. On the other hand, if the predetermined movement magnitude threshold has been established as 2.0 cm, the control system will determine that the movement magnitude does not exceed the movement magnitude threshold. In response, an indication that an image capture procedure may be initiated may be provided to a user or to an intra-operative imaging system.

FIG. 5 illustrates a method 500 for synchronizing a robot-assisted medical system with an imaging system during an image capture period of the imaging system to coordinate process 216 of FIG. 2 with the image capture procedure that generates the intra-operative image data of process 214. During a synchronized image capture period, two different representations of a physical entity, for example a medical instrument, may be recorded. One representation may be the three-dimensional image of the instrument generated by the imaging system, and one representation may be the three-dimensional shape generated by the shape sensor disposed within the instrument.

At a process 502, a communication signal (e.g., a timing signal or an initiation signal) may be generated. The communication signal may include synchronization information which may include start and/or stop signals, clock signals, synchronization protocol information, image capture period duration information, or other information for synchronizing a medical system including the instrument and an imaging system. For example, the communication signal may be generated by a communication device of the control system or by a communication device of the imaging system.

At a process 504, the communication signal may be sent between the medical system and the imaging system. For example, the communication signal may be sent from the imaging system to the medical system or from the medical system to the imaging system.

At a process 506, based on the synchronization information from the communication signal, the recording of shape data from an instrument shape sensor of the medical system is synchronized with the recording of image data from the imaging system during an image capture period. Because the medical and imaging systems are synchronized, the image data and the shape data are recorded over a common period of time. Both the shape data and the image data may be recorded while the medical instrument, including the instrument shape sensor, is located within the imaged anatomy of the patient. With the data collection periods for the shape sensor and the imaging system synchronized, two different representations of the medical instrument are recorded. The image data, including an image of the shape of the instrument, can be matched to the shape sensor data, describing the shape of the same instrument, for the exact same time period. As described further below, the matched data sets may be used for registration of the image reference frame $(X_I, Y_I, Z_I)$ with the medical instrument reference frame $(X_M, Y_M, Z_M)$.

In various examples, a communication signal may be sent simultaneously with initiation of the scan or may be indicative of a future scan start time (e.g., 1 second, 10 seconds) so that shape data from the shape sensor may begin recording simultaneously with the initiation of the image capture period. The communication signal may originate from an application programming interface of the intra-operative imaging system. As an example, the Cios Spin® imaging system marketed by Siemens® Medical Solutions USA, Inc. utilizes a protocol called NaviLink 3D™ which provides a digital interface to connect the imaging system with navigation systems and transfer datasets thereto. Similarly, a communication signal may be sent in conjunction with the termination of the intra-operative scan so that the control system may cease recording shape data. In some embodiments, the shape data may be recorded over a longer interval than the image capture period and the communication signal(s) may be used to earmark certain data points in the shape data corresponding to the image capture period. In some embodiments, the communication signal(s) may be sent from the control system of the instrument to the imaging system to instruct the imaging system when to start and stop the scan. In some instances, in lieu of communication signals, the image data from the imaging system may be streamed to the control system of the medical instrument in substantially real-time such that recording of the shape data may coincide with the beginning and the end of the transmission/receipt of the streamed data. In this regard, when the first image data from the image capture period is received at the control system of the medical instrument, the control system may begin recording shape data. Similarly, when the control system stops receiving the stream of image data, the control system may stop recording shape data.

In one embodiment, the clock of the medical system is synchronized to the clock of the imaging system during an image capture period. A communication signal including synchronization information for synchronizing the clocks may be sent between the medical system and the imaging system. The synchronization of the clocks may occur just before initiation of the image capture period or with the initiation of the image capture period. The synchronization may occur once or may be repeated one or more times during the image capture period. In some embodiments, the synchronization of the clocks may be achieved by wired or wireless communication between the communication devices connected either directly or over a network.

In another embodiment, the medical system is synchronized with the imaging system by start and stop signals. The communication signal, including synchronization information in the form of a start signal, may be sent between the medical system and the imaging system. The start signal may initiate, occur simultaneously with, or be triggered by the start the image capture period during which image data is recorded by the imaging system. The receipt or sending of the start signal may also initiate recording or mark a starting point in a longer recording of shape data for the instrument system of the medical system. At the end of the image capture period, another communication signal, including synchronization information in the form of a stop signal, may be sent between the medical system and the imaging system. The stop signal may initiate, occur simultaneously with, or be triggered by the stopping of the image capture period during which image data is recorded by the imaging system. The receipt or sending of the stop signal may also terminate recording or mark a termination point in a longer recording of shape data for the instrument system of the medical system.

In some embodiments, the recording of shape data may be initiated by a user command. For example, a user(s) may simultaneously input a command on the imaging system and the instrument to initiate the imaging scan and the recording of the shape data. Similarly, the user(s) may simultaneously input a command to stop the imaging scan and the recording of the shape data. Such a command may be input by any suitable means such as pressing a button, stating a voice command, etc. In some instances, the image capture period may be known in advance such that the control system may start recording the shape data upon receipt of the command and stop recording the shape data once the image capture period has elapsed, or at some point in time thereafter. For example, if the image capture period is known to be 20-30 seconds, the control system may record the shape data for 30 or more seconds to ensure shape data for the entire image capture period is recorded. When shape data for a relatively large window of time is desired, the shape data may be stored in a large buffer.

In some embodiments, the recording of shape data may be initiated automatically upon a determination by the control system of the instrument that the instrument is parked in close proximity to the location of the target as determined by the pre-operative image data. Alternatively, shape data from the instrument may be monitored and the recording of the shape data may begin in response to a determination that a breath-hold has been initiated. For example, the shape data may indicate movement of the instrument with the anatomical passageways during cyclical motion caused by breathing but may then indicate that the instrument has substantially stopped moving, thereby suggesting that a breath hold has by initiated via breathing tube. Parking of the instrument near the target and/or a breath-hold may be interpreted as an indication that the intra-operative imaging scan is beginning or will begin soon thereafter.

Figure 6:
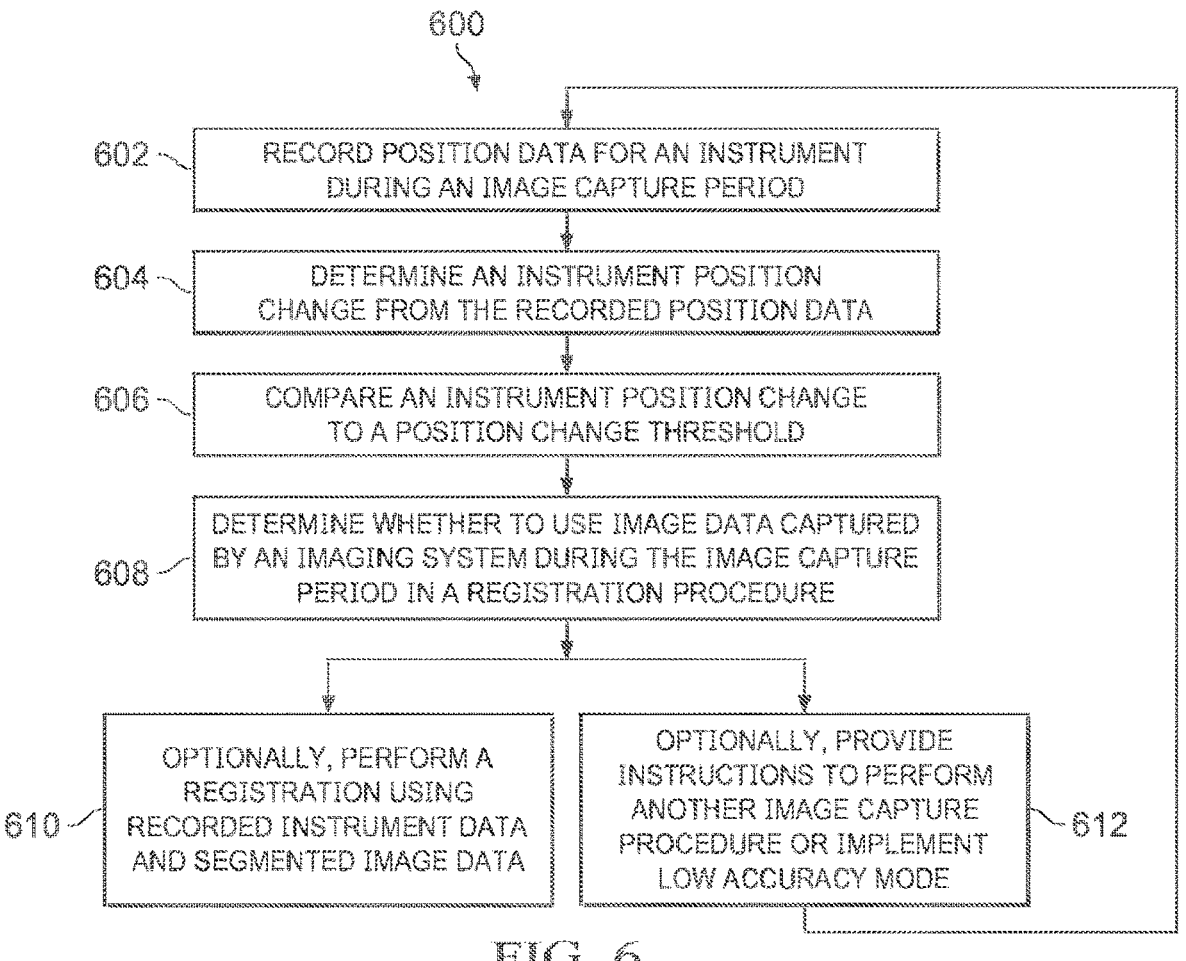
FIG. 6 illustrates a method for evaluating image data for use in a registration procedure.

In some embodiments, after the determination has been made to initiate the image capture as described in FIGS. 3 and 4, the medical system and imaging system are synchronized as described in FIG. 5, and intra-operative imaging has been performed, a determination may be made as to whether the image data is suitable for use in registration based upon the shape data received in process 216 of FIG. 2. FIG. 6 illustrates a method 600 for evaluating anatomic image data for use in a registration procedure. Often, anatomic motion can result in intra-operative anatomic image data that is too distorted to isolate and segment the medical instrument. Before attempting to register the intra-operative image to the medical instrument, a change in the position of the medical instrument, or a portion of the medical instrument, may be evaluated over the image capture period. If the position of the medical instrument changes in excess of a threshold amount, the captured image may be considered inadequate for use in registration or may warrant implementation of the low accuracy mode. In some instances, if the shape data indicates a position change which is particularly problematic, instructions may be provided to initiate a new image capture procedure.

At a process 602, position data is recorded for an instrument (e.g. medical instrument 104) during an image capture period of an imaging system. In some embodiments, an image capture period corresponds to the time period during which an intra-operative imaging system is activated to collect and record image data for a patient. During that time period, shape data for the instrument may be recorded. For example, shape data gathered from a shape sensor may provide position information for the instrument and a plurality of points along the instrument in the medical instrument reference frame $(X_M, Y_M, Z_M)$, which is known relative to the surgical reference frame $(X_S, Y_S, Z_S)$. During the time period, the instrument may be subject to no commanded movement, such as automated or operator-commanded advancement or bending, but may be subject to unintended movement such as anatomic motion from breathing, cardiac activity, or other voluntary or involuntary patient motion. For example, an image scan may be performed with the intra-operative imaging system over an image capture period while the instrument is positioned within the patient anatomy, without being subject to commanded motion.

At a process 604, a position change associated with at least a portion of the instrument during the image capture period is determined from the recorded shape data. For example, shape data at a beginning of an image capture period is compared to shape data at an end of the image capture period or distal end position data at a beginning of an image capture period is compared to distal end position data at an end of the image capture period. In some embodiments, shape data may be utilized to determine a position change for the whole instrument (e.g., a lateral translation) or for a segment of the instrument less than the entire length (e.g., a bend near the distal end or tip). In some embodiments, the shape data may be measured and recorded continuously at regular intervals, such as once per second or 100 times per second. In some embodiments, shape data may be monitored continuously but only recorded when a change in shape is detected.

At a process 606, the determined change in an instrument position during the image capture period is compared to a position change threshold. For example, if a determined position change of a distal end of the instrument is 1 cm and the position change threshold is approximately 2 cm, the position change does not reach the threshold. If the determined position change is 3 cm and the position change threshold is 2 cm, the position change has exceeded the threshold. In some embodiments, the position change threshold may be established in one, two, or three dimensions or a combination thereof, with the same or different threshold values in the different dimensions. In some embodiments, the comparison may also include comparisons of orientation and shape. In various embodiments, the position change threshold may be greater or less than 2 cm. In various embodiments, the position change threshold may be a threshold based on, for example, a maximum position change, an average position change, or a standard deviation for the position change.

At a process 608, a determination is made as to whether the image data captured by the imaging system during the image capture period may be used in a registration procedure to register the image reference frame to the medical instrument reference frame and/or the surgical reference frame. If the instrument, or a portion thereof, is determined to have moved too much (e.g., in excess of the position change threshold), discrepancies between the image data from the intra-operative imaging system and the shape data from the instrument may prevent registration of the image reference frame to the medical instrument reference frame and/or the surgical reference frame. In this case, a determination would be made to not use the image data for a registration procedure or a low accuracy mode would be implemented to restrict registration to translation only. For example, if the instrument position change is 3 cm, exceeding the position change threshold of 2 cm, this may indicate that instrument moved too much during the image capture period, and the image data generated by the intra-operative imaging system may be too distorted to provide an accurate registration to the instrument shape data gathered during the image capture period. If, however, the change in instrument position is 1 cm, below the position change threshold of 2 cm, this may indicate that the position change of the instrument was within an acceptable range, and the image data generated by the intra-operative imaging system may be used for registration. In some embodiments, control signals sent to the instrument may be evaluated to determine if commanded movement, such as automated or operator-commanded advancement or bending, occurred during the image capture period. If a determination is made that commanded motion did occur, the image data may be discarded, suppressed, or otherwise not used for registration. In some instances, a magnitude and direction of the commanded movement may be determined and the position change may be negated by altering the shape data based upon the magnitude and direction of the commanded movement.

At an optional process 610, if the image data is determined to be acceptable for use in registration, the registration may be performed. In some embodiments, as part of a registration process, image units, such as pixels or voxels, in the image data from the imaging system that correspond to the medical instrument are identified. In some embodiments, computer software, alone or in combination with manual input, is used to convert the image data into a segmented two-dimensional or three-dimensional composite representation or model of a partial or an entire anatomic organ or anatomic region. The model may describe the various locations and shapes of the anatomic passageways and their connectivity. More specifically, during the segmentation process the pixels or voxels may be partitioned into segments or elements or be tagged to indicate that they share certain characteristics or computed properties such as color, density, intensity, and texture. The image data corresponding to the image of the medical instrument may be segmented or filtered out of the image data, and a model of the instrument shape may be generated. For example, the medical instrument may be identified as a medical instrument in the image data by the segmentation or filtering by CT number or Hounsfield value associated with the medical instrument. This data associated with the medical instrument may be isolated from other portions of the image data that are associated with the patient or with specific tissue types. A three-dimensional mesh model may be formed around the isolated data and/or a centerline may be determined that represents a centerline of the medical instrument. The segmented image data for the instrument may be expressed in the image reference frame.

The segmented shape of the medical instrument may be registered with the shape data obtained from the medical instrument during the image capture period. The shape data from the medical instrument may be expressed in the medical instrument reference frame and/or the surgical reference frame. This registration may rotate, translate, or otherwise manipulate by rigid or non-rigid transforms points associated with the segmented shape and points associated with the shape data. This registration between the model and instrument frames of reference may be achieved, for example, by using ICP or another point cloud registration technique. In some embodiments, the segmented shape of the medical instrument is registered to the shape data and the associated transform (a vector applied to each of the points in the segmented shape to align with the shape data in the shape sensor reference frame) may then be applied to the entire three-dimensional image and/or to subsequently obtained three-dimensional images during the medical procedure. The transform may be a six degrees-of-freedom (6DOF) transform, such that the shape data may be translated or rotated in any or all of X, Y, and Z and pitch, roll, and yaw.

With the image reference frame registered to the medical instrument reference frame, the images displayed to the operator on the display system may allow the operator to more accurately steer the medical instrument, visualize a target lesion relative to the medical instrument, observe a view from the perspective of a distal end of the medical instrument, and/or improve efficiency and efficacy of targeted medical procedures.

In some embodiments, the intra-operative image data may be registered with pre-operative image data obtained by the same or a different imaging system. Thus, by registering the shape data to the intra-operative image data, the registration of the shape data to the pre-operative image data may also be determined. In some embodiments, an anatomic image generated from the intra-operative image data and/or the pre-operative image data may be displayed with the image of the instrument derived from the instrument shape sensor data. For example, a model of the instrument generated from the instrument shape data may be superimposed on the image of the patient anatomy generated from the pre-operative or intra-operative image data.

At an optional process 612, if the image data is determined to be unacceptable for use in registration, the registration procedure may be aborted. Instructions may be provided to a user to initiate a new image capture procedure or the control system may initiate the new image capture procedure.

Figure 7A:
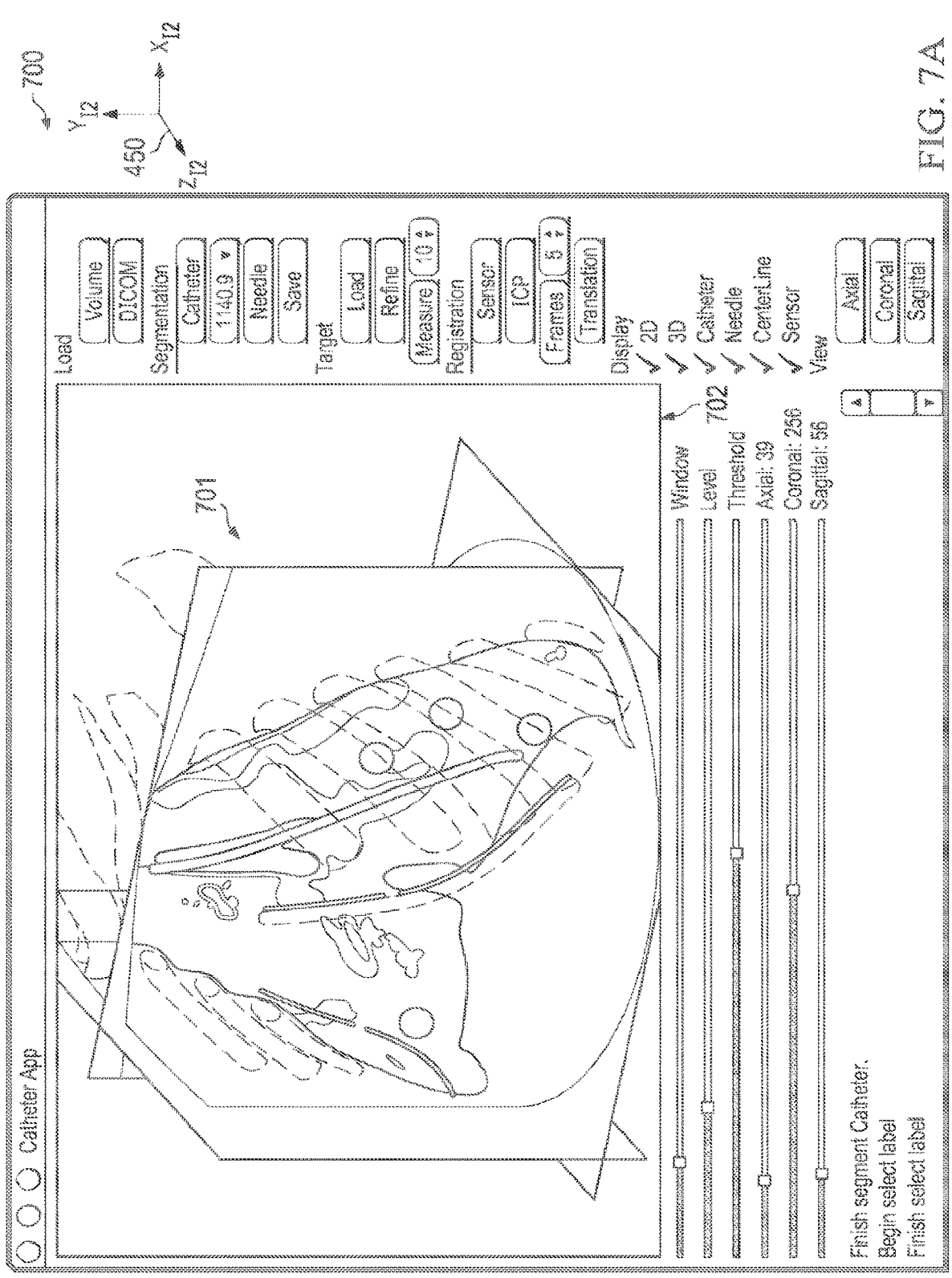
FIG. 7A illustrates a simplified diagram of a user interface displaying image data from an intra-operative imaging procedure.

In some embodiments, the intra-operative image data received at process 214 of FIG. 2 may be displayed on a user interface 700 of a display system as shown in FIG. 7A. A viewing mode 702 may provide a 3D rendering 701 of the intra-operative image data in an intra-operative image reference frame $(X_{I2}, Y_{I2}, Z_{I2})$ 450. Pixels or voxels may be displayed with assigned intensity values which provide an initial visual demarcation between distinct structures.

Figure 7B:
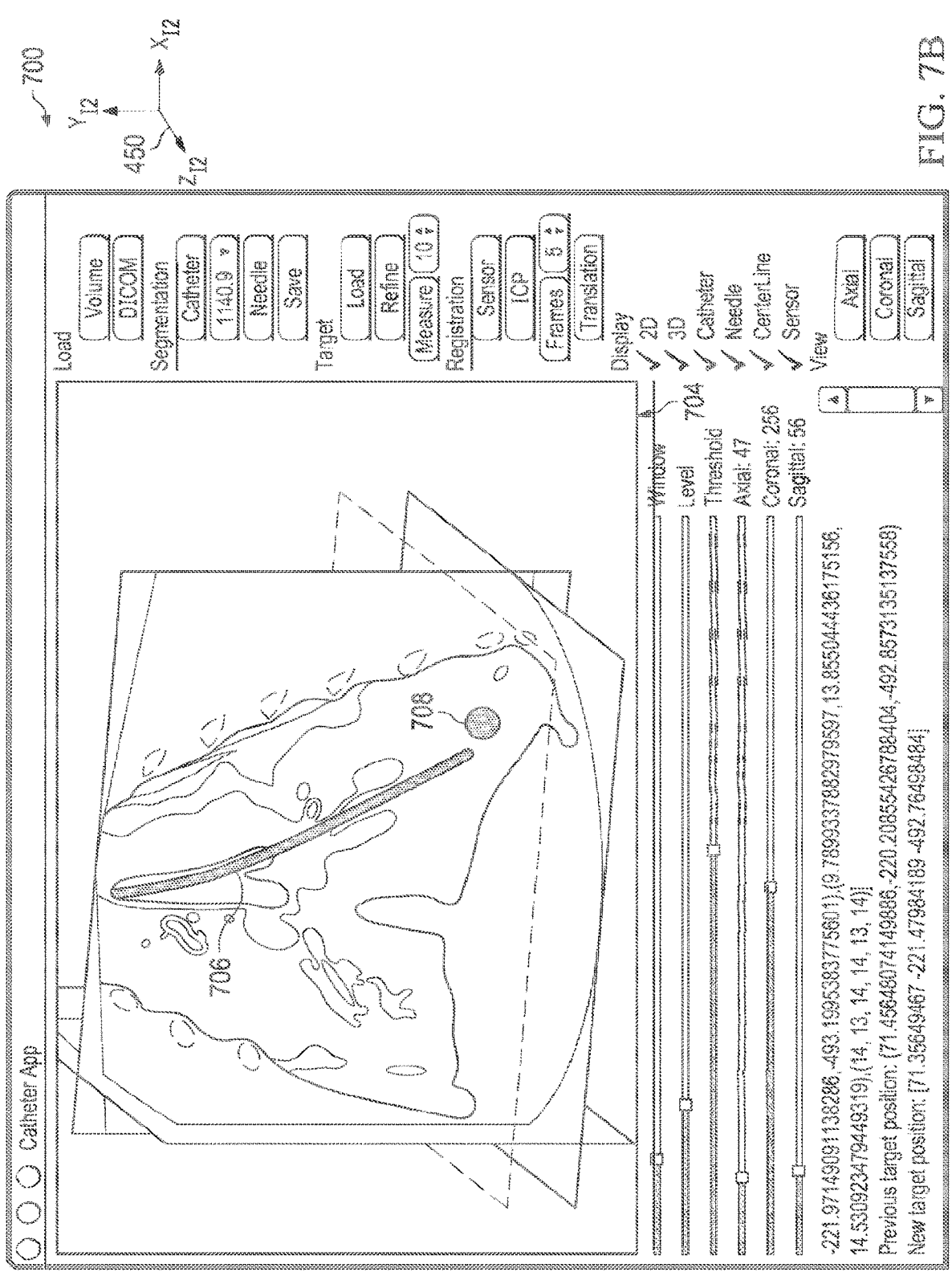
FIG. 7B illustrates a simplified diagram of a user interface displaying image data from an intra-operative imaging procedure in which an instrument and a target have been segmented.

Following the segmentation process 218 of FIG. 2 the segmented instrument may be displayed in conjunction with the intra-operative image data on the display system. Similarly, following the identification of the target at process 220 of FIG. 2, the segmented target may be displayed in conjunction with the intra-operative image data on the display system. FIG. 7B illustrates a viewing mode 704 providing a two-dimensional and/or three-dimensional view of the intra-operative image data in which the instrument 706 and target 708 have been segmented. The viewing mode 704 may display the segmented instrument centerline and/or boundary registered to the 3D model. When segmentation is unsuccessful, the user interface 700 may allow a user to manually identify the catheter and/or the target. Following segmentation or identification, the instrument 706 and target 708 may be displayed in a different color or otherwise visually distinguished from surrounding anatomical structures.

Figures 8A, 8B:
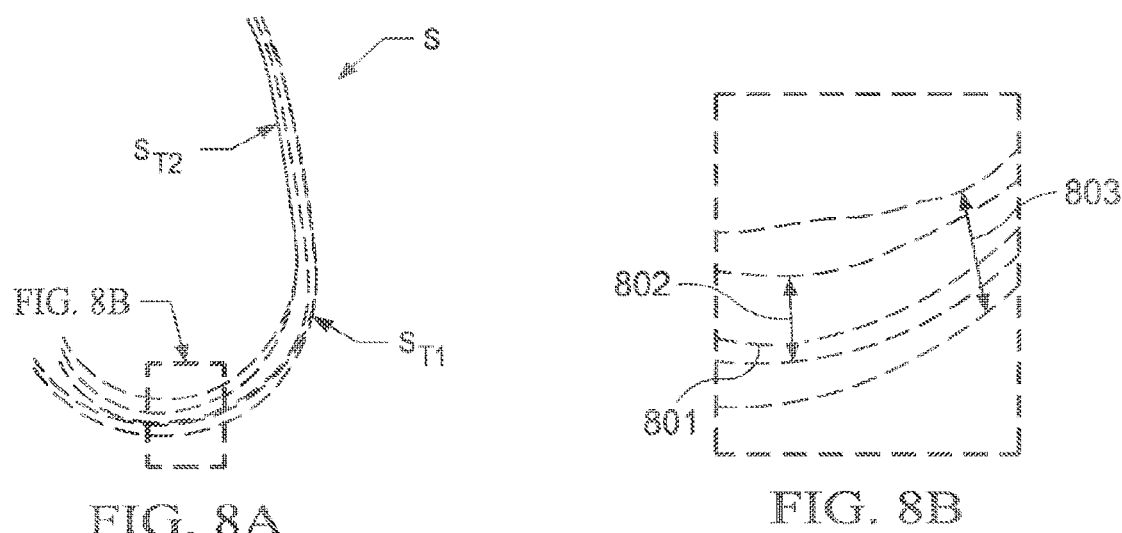
FIG. 8A illustrates shape data indicating motion of an instrument during an imaging procedure.
FIG. 8B illustrates a detailed view of a section of the illustration of FIG. 8A.

Upon segmentation or identification of the instrument 706 in the intra-operative image data, the intra-operative image reference frame 450 may be registered to the medical instrument reference frame, as discussed above in relation to process 222 of FIG. 2. In some embodiments, this registration may be performed using a weighted ICP technique as discussed with reference to FIGS. 8A and 8B. FIGS. 8A and 8B illustrate a set of shape data S (which may include a number of data points), corresponding to the shape of the instrument in the medical instrument reference frame, gathered during the image capture period. Due to anatomical motion, the shape data S may have a configuration $S_{T1}$ at a time T1 during the image capture period and may have a configuration $S_{T2}$ at a time T2 during the image capture period. Any number of additional configurations of the instrument may extend between $S_{T1}$ and $S_{T2}$. Moreover, $S_{T1}$ and $S_{T2}$ may correspond to shape extrema during the image capture period or may be any two arbitrary configurations of the instrument during the image capture period. FIG. 8B illustrates a portion of the shape data S. Because the shape data S indicates that the instrument was moving during the image capture period, one or more portions of the shape data may be better suited for registration than other portions of the shape data. In this regard, the one or more portions of the shape data may be weighted more heavily than one or more other portions of the shape data.

In some embodiments, various portions of the shape data may be weighted with a weight value ranging from 0 to 1, in which a value of 0 indicates a particular data point will not affect the registration, a value of 1 indicates a particular data point will be fully weighted in registration, and a value between 0 and 1 indicates a particular data point will affect the registration but will not be fully weighted. In some embodiments, one or more portions of the shape data may be weighted with a negative value and other portions may be weighted with a value exceeding 1.

The set of shape data S may be evaluated to determine a baseline (e.g., using an average or standard deviation) of the instrument shape data. As shown in FIG. 8B, data points nearest a determined baseline 801 may be weighted most heavily (e.g., 1). Data points outside the range 803 may be considered outliers and may be discarded or weighted 0. Data points within the zone associated with range 803 may be weighted with a relatively small value (e.g., 0.5) and data points in the zone associated with range 802 may be associated with a relatively larger value (e.g., 0.9). Any of number of zones may be utilized and dimensions of the zones may be predetermined and retrieved from memory or may be calculated based upon factors determined from the set of shape data (e.g., average, number of data points, standard deviation, etc.).

In some embodiments, the set of shape data S may be filtered to generate an instrument shape which corresponds to an instrument shape provided by intra-operative image data (which may be an average of the observed location). For example, if the image data indicates a shape resembling the configuration of $S_{T1}$, the data corresponding to $S_{T2}$ may be filtered out or weighted insignificantly.

Figure 9:
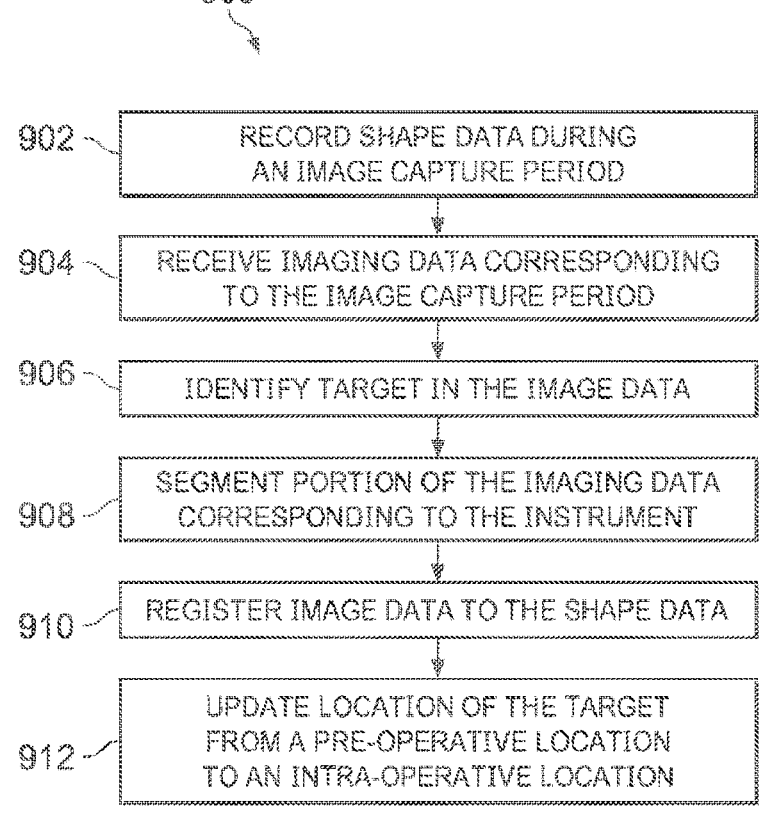
FIG. 9 illustrates a method of registering image data to shape data from an instrument to update a location of a target in a model.

As discussed above with reference to process 226 in FIG. 2, a target location may be updated from a location based on pre-operative image data to a location based on intra-operative image data. FIG. 9 illustrates a method 900 of registering intra-operative image data to shape data from an instrument to update a location of a target in a model. At a process 902, instrument shape data may be recorded during an image capture period of an imaging system. The imaging system may be cone beam CT system or any other imaging system configured for capturing intra-operative images of an instrument and patient anatomy. At a process 904, image data corresponding to the image capture period may be received, the image data including the patient's anatomy, the target of the procedure, and the instrument. At a process 906, the target is identified in the image data. For example, the target may be segmented by the control system or other processing platform or may be manually identified by a user. At a process 908, a portion of the image data corresponding to the instrument may be segmented. Using the segmented image data and the shape data recorded in process 902, the image data may be registered to the shape data based upon the shape of the instrument during the image capture period at a process 910. At a process 912, using the registered image data, the location of the target may be updated from a pre-operative location based upon pre-operative imaging to an intra-operative location based upon the intra-operative imaging, as discussed below with reference to FIG. 11. The updated target location may improve navigation of the instrument to the target.

Similar to the process 226 for updating a location of a target in the image reference frame, an additional or alternative process may be used to update a location of an anatomical passage in the image reference frame. FIG. 10 illustrates a method 1000 of registering intra-operative image data to shape data from an instrument to update a location of an anatomic structure in a model. At a process 1002, instrument shape data may be recorded during an image capture period of an imaging system. The imaging system may be cone beam CT system or any other imaging system configured for capturing intra-operative images of an instrument and patient anatomy. At a process 1004, image data corresponding to the image capture period may be received, the image data including the patient's anatomy, the target of the procedure, and the instrument. At a process 1006, the target is identified in the image data. For example, the target may be segmented by the control system or other processing platform or may be manually identified by a user. At a process 1008, a portion of the image data corresponding to the instrument may be segmented and, at a process 1010, portions of the image data corresponding to anatomical passageways may be segmented. Using the segmented image data and the shape data recorded in process 1002, the image data may be registered to the shape data based upon the shape of the instrument during the image capture period at a process 1012. At a process 1014, using the registered image data, the location of one or more anatomical passageways may be updated from a pre-operative location based upon pre-operative imaging to an intra-operative location based upon the intra-operative imaging, as discussed below with reference to FIG. 11. Updating of the one or more passageways may provide a more accurate path from a current location of the instrument to the target. It should be appreciated that method 900 and method 1000 are both optional and may be performed simultaneously or consecutively.

Figure 11:
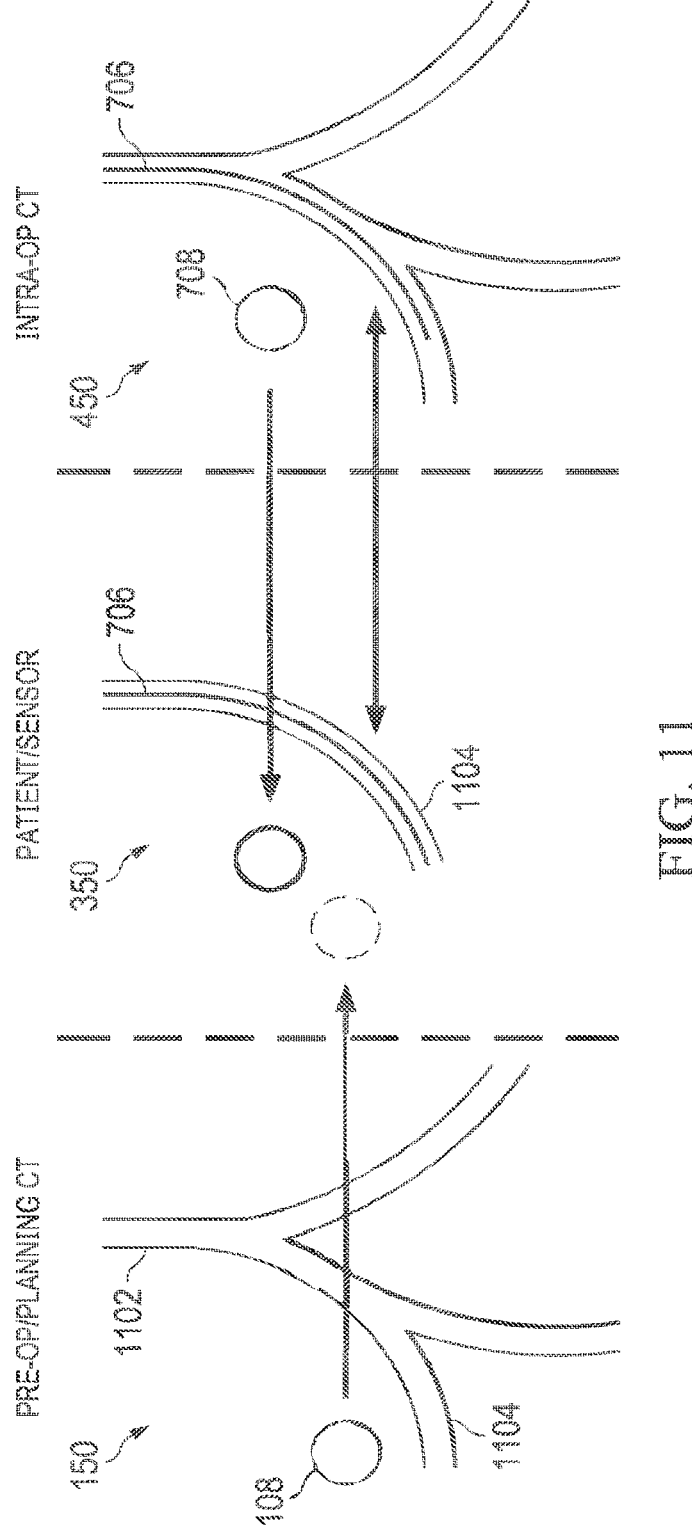
FIG. 11 illustrates a simplified diagram of registering pre-operative image data and intra-operative image data to shape data from an instrument.

As discussed above in relation to process 210 in FIG. 2, an image reference frame of pre-operative image data may be registered to an instrument reference frame. Similarly, an intra-operative image reference frame may be registered to the instrument reference frame as discussed above in relation to process 222. The common registration between these reference frames allows for updating of the target in the 3D model. FIG. 11 provides a simplified diagram of registering pre-operative image data in an image reference frame 150 and intra-operative image data in an intra-operative image reference frame 450 to shape data from an instrument in a medical instrument reference frame 350 (which may also be registered to a surgical reference frame 250 in which a patient is positioned). Initially, a 3D model 1102 may be constructed from pre-operative image data. The model may include anatomical passageway 1104 and a pre-operative location of target 108 disposed relative to anatomical passageway 1104. During a medical procedure, an instrument 706 including a shape sensor may be inserted into anatomical passageway 1104. Based on the shape of anatomical passageway 1104 in the pre-operative image data and shape data from the shape sensor, the image reference frame 150 may be registered to the medical instrument reference frame 350. Additionally, while the instrument 706 is disposed within anatomical passageway 1104, intra-operative imaging may be obtained, for example, using cone beam CT. The intra-operative image data may indicate a location of target 708 relative to instrument 706 in the intra-operative image reference frame 450. Using the shape of the instrument 706 in the intra-operative image data and the shape data from the shape sensor, the intra-operative image reference frame 450 may be registered to the medical instrument reference frame 350. Accordingly, the image reference frame 150 and the intra-operative image reference frame 450 may also be registered. This registration arrangement allows for the pre-operative location of the target 108 to be updated to the intra-operative location of the target 708 as described above with reference to FIG. 9, and anatomical passages in a model to be updated as described above with reference to FIG. 10.

Figure 12A:
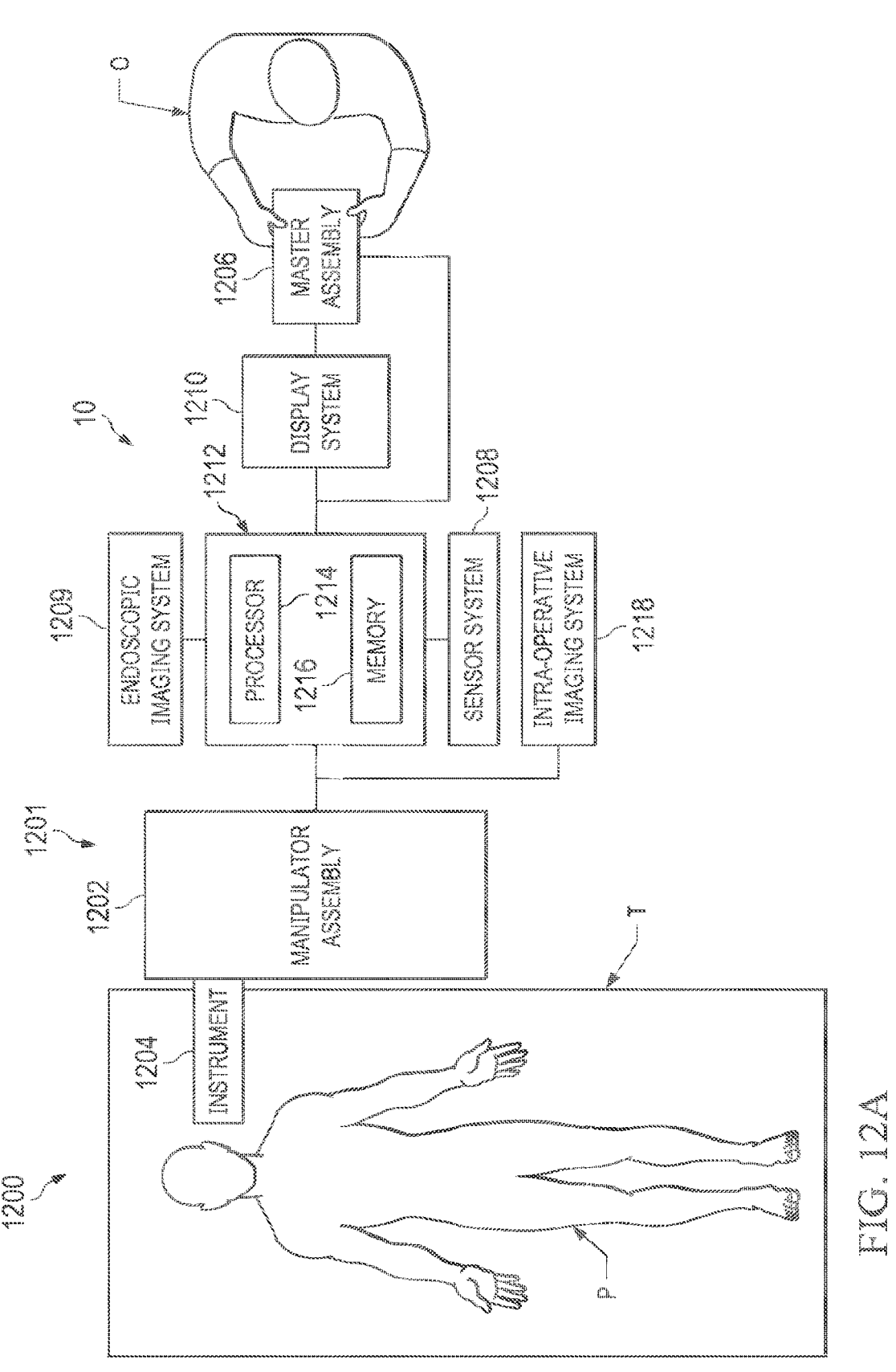
FIG. 12A illustrates a simplified diagram of a robot-assisted medical system according to some embodiments.
Figure 12B:
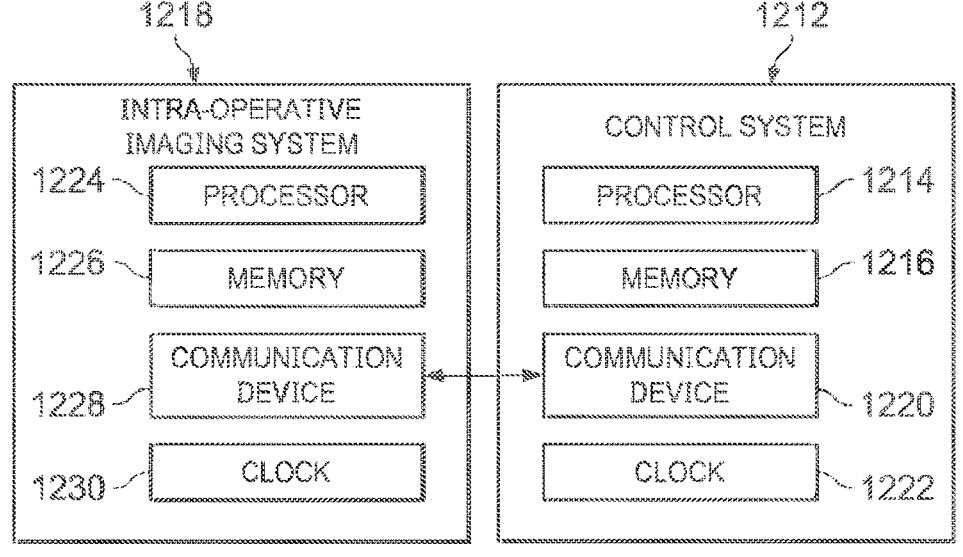
FIG. 12B illustrates communication between a control system and an intra-operative imaging system.
Figure 13:
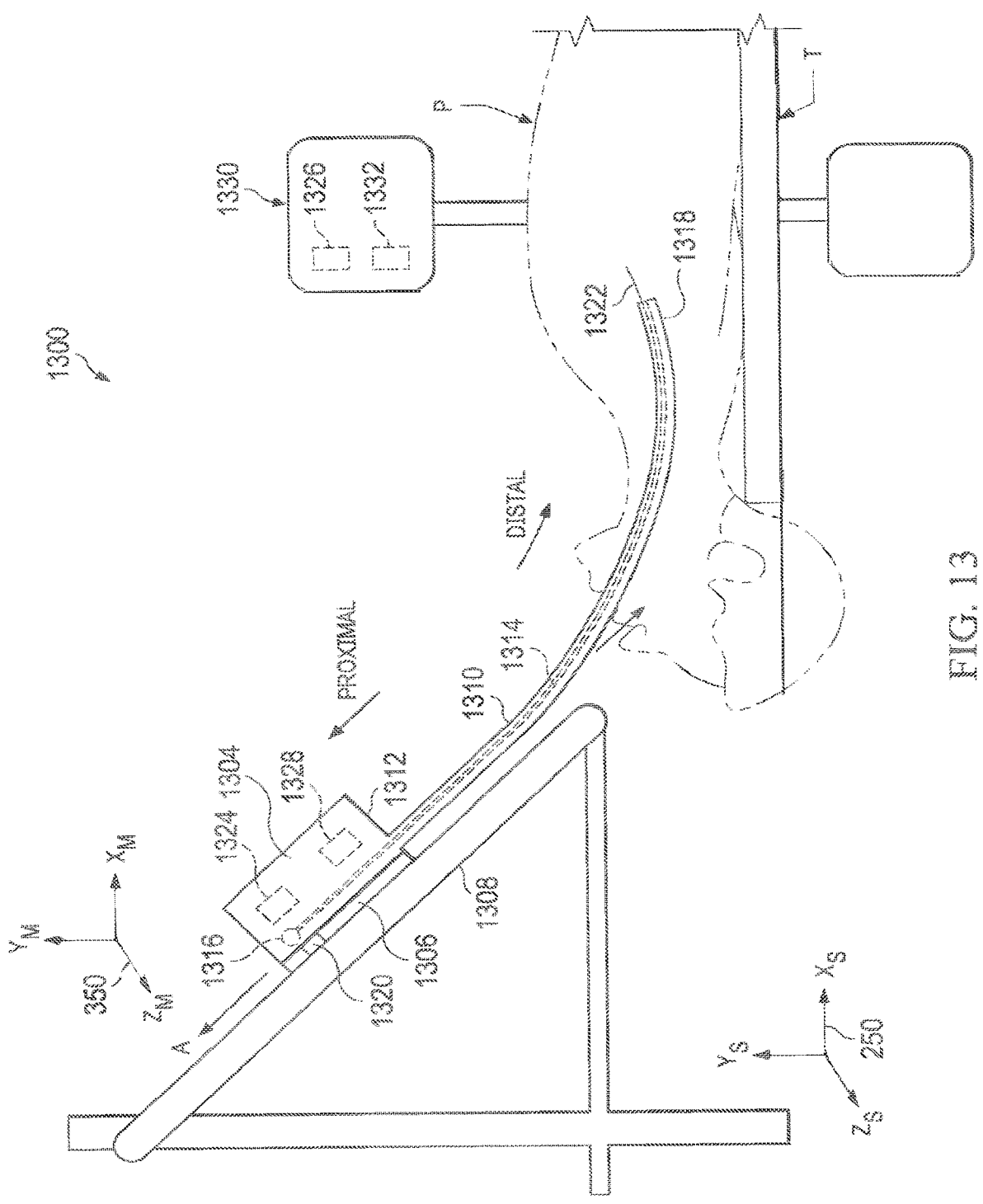
FIG. 13 illustrates a simplified diagram of a medical instrument system and an intraoperative imaging system according to some embodiments.

In some embodiments, the registration techniques of this disclosure, such as those discussed in relation to processes 210 and 222 of FIG. 2, may be used in an image-guided medical procedure performed with a robot-assisted medical system as shown in FIGS. 12A-13. FIG. 12A illustrates a clinical system 10 includes a robot-assisted medical system 1200 and an intra-operative imaging system 1218. The robot-assisted medical system 1200 generally includes a manipulator assembly 1202 for operating a medical instrument system 1204 (including, for example, medical instrument 104) in performing various procedures on a patient P positioned on a table T in a surgical environment 1201. The manipulator assembly 1202 may be robot-assisted, non-assisted, or a hybrid robot-assisted and non-assisted assembly with select degrees of freedom of motion that may be motorized and/or robot-assisted and select degrees of freedom of motion that may be non-motorized and/or non-assisted. A master assembly 1206, which may be inside or outside of the surgical environment 1201, generally includes one or more control devices for controlling manipulator assembly 1202. Manipulator assembly 1202 supports medical instrument system 1204 and may optionally include a plurality of actuators or motors that drive inputs on medical instrument system 1204 in response to commands from a control system 1212. The actuators may optionally include drive systems that when coupled to medical instrument system 1204 may advance medical instrument system 1204 into a naturally or surgically created anatomic orifice. Other drive systems may move the distal end of medical instrument system 1204 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument system 1204 for grasping tissue in the jaws of a biopsy device and/or the like.

Robot-assisted medical system 1200 also includes a display system 1210 (which may the same as display system 100) for displaying an image or representation of the surgical site and medical instrument system 1204 generated by a sensor system 1208 and/or an endoscopic imaging system 1209. Display system 1210 and master assembly 1206 may be oriented so operator O can control medical instrument system 1204 and master assembly 1206 with the perception of telepresence.

In some embodiments, medical instrument system 1204 may include components for use in surgery, biopsy, ablation, illumination, irrigation, or suction. Optionally medical instrument system 1204, together with sensor system 1208 may be used to gather (i.e., measure) a set of data points corresponding to locations within anatomic passageways of a patient, such as patient P. In some embodiments, medical instrument system 1204 may include components of the imaging system 1209, which may include an imaging scope assembly or imaging instrument that records a concurrent or real-time image of a surgical site and provides the image to the operator or operator O through the display system 1210. The concurrent image may be, for example, a two or three-dimensional image captured by an imaging instrument positioned within the surgical site. In some embodiments, the imaging system components that may be integrally or removably coupled to medical instrument system 1204. However, in some embodiments, a separate endoscope, attached to a separate manipulator assembly may be used with medical instrument system 1204 to image the surgical site. The imaging system 1209 may be implemented as hardware, firmware, software or a combination thereof which interact with or are otherwise executed by one or more computer processors, which may include the processors of the control system 1212.

The sensor system 1208 may include a position/location sensor system (e.g., an electromagnetic (EM) sensor system) and/or a shape sensor system for determining the position, orientation, speed, velocity, pose, and/or shape of the medical instrument system 1204.

Robot-assisted medical system 1200 may also include control system 1212. Control system 1212 includes at least one memory 1216 and at least one computer processor 1214 for effecting control between medical instrument system 1204, master assembly 1206, sensor system 1208, endoscopic imaging system 1209, and display system 1210. Control system 1212 also includes programmed instructions (e.g., a non-transitory machine-readable medium storing the instructions) to implement some or all of the methods described in accordance with aspects disclosed herein, including instructions for providing information to display system 1210.

Control system 1212 may optionally further include a virtual visualization system to provide navigation assistance to operator O when controlling medical instrument system 1204 during an image-guided surgical procedure. Virtual navigation using the virtual visualization system may be based upon reference to an acquired pre-operative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

An intra-operative imaging system 1218 may be arranged in the surgical environment 1201 near the patient P to obtain images of the patient P during a medical procedure. The intra-operative imaging system 1218 may provide real-time or near real-time images of the patient P. In some embodiments, the intra-operative imaging system 1218 may be a mobile C-arm cone-beam CT imaging system for generating three-dimensional images. For example, the intra-operative imaging system 1218 may be a DynaCT imaging system from Siemens Corporation of Washington, D.C., or other suitable imaging system. In other embodiments, the imaging system may use other imaging technologies including CT, MRI, fluoroscopy, thermography, ultrasound, optical coherence tomography (OCT), thermal imaging, impedance imaging, laser imaging, nanotube X-ray imaging, and/or the like.

FIG. 12B illustrates communication between the control system 1212 and the intra-operative imaging system 1218. In some embodiments, the control system 1212 includes a communication device 1220 and a clock 1222. Although the control system 1212 is shown as a single block in the simplified schematics of FIGS. 12A and 12B, the control system 1212 may include multiple processors, memories, communication devices, and clocks. Furthermore, the components of the control system 1212 may be distributed throughout the medical system 1200, including at the manipulator assembly 1202, the instrument system 1204 and the master assembly 1206. In some embodiments, the intra-operative imaging system includes a processor 1224, a memory 126, a communication device 1228, and a clock 1230. The processor 1224 is configured to execute programmed instructions stored, for example, on memory 1226 to implement some or all of the methods described in accordance with aspects disclosed herein. The clocks 1222, 1230 may include any type of digital clock, analog clock, software-based clock, or other timekeeping device. The communication devices 1220, 1228 may include information transmitters, information receivers, information transceivers or a combination of transmitting or receiving devices that enable wired or wireless communication between the imaging system 1218 and the control system 1212 and/or between the clocks 1222, 1230. The communication devices 1220, 1228 may be used to exchange information between the two systems including, for example, clock signals, start and stop signals, image data signals, patient data signals, and sensor data signals.

FIG. 13 illustrates a surgical environment 1300 with a surgical reference frame $(X_S, Y_S, Z_S)$ 250 in which the patient P is positioned on the table T. Patient P may be stationary within the surgical environment in the sense that gross patient movement is limited by sedation, restraint, and/or other means. Cyclic anatomic motion including respiration and cardiac motion of patient P may continue unless the patient is asked to hold his or her breath to temporarily suspend respiratory motion. Within surgical environment 1300, a medical instrument 1304 (e.g., the medical instrument system 1204), having a medical instrument reference frame $(X_M, Y_M, Z_M)$ 350, is coupled to an instrument carriage 1306. In this embodiment, medical instrument 1304 includes an elongate device 1310, such as a flexible catheter, coupled to an instrument body 1312. Instrument carriage 1306 is mounted to an insertion stage 1308 fixed within surgical environment 1300. Alternatively, insertion stage 1308 may be movable but have a known location (e.g., via a tracking sensor or other tracking device) within surgical environment 1300. In these alternatives, the medical instrument reference frame is fixed or otherwise known relative to the surgical reference frame. Instrument carriage 1306 may be a component of a robot-assisted manipulator assembly (e.g., robot-assisted manipulator assembly 1302) that couples to medical instrument 1304 to control insertion motion (i.e., motion along an axis A) and, optionally, motion of a distal end 1318 of the elongate device 1310 in multiple directions including yaw, pitch, and roll. Instrument carriage 1306 or insertion stage 1308 may include actuators, such as servomotors, (not shown) that control motion of instrument carriage 1306 along insertion stage 1308.

In this embodiment, a sensor system (e.g., sensor system 1208) includes a shape sensor 1314. Shape sensor 1314 may include an optical fiber extending within and aligned with elongate device 1310. In one embodiment, the optical fiber has a diameter of approximately 200 μm. In other embodiments, the dimensions may be larger or smaller. The optical fiber of shape sensor 1314 forms a fiber optic bend sensor for determining the shape of the elongate device 1310. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the catheter may be determined using other techniques. For example, a history of the distal end pose of elongate device 1310 can be used to reconstruct the shape of elongate device 1310 over the interval of time.

As shown in FIG. 13, instrument body 1312 is coupled and fixed relative to instrument carriage 1306. In some embodiments, the optical fiber shape sensor 1314 is fixed at a proximal point 1316 on instrument body 1312. In some embodiments, proximal point 1316 of optical fiber shape sensor 1314 may be movable along with instrument body 1312 but the location of proximal point 1316 may be known (e.g., via a tracking sensor or other tracking device). Shape sensor 1314 measures a shape from proximal point 1316 to another point such as distal end 1318 of elongate device 1310 in the medical instrument reference frame $(X_M, Y_M, Z_M)$.

Elongate device 1310 includes a channel (not shown) sized and shaped to receive a medical instrument 1322. In some embodiments, medical instrument 1322 may be used for procedures such as surgery, biopsy, ablation, illumination, irrigation, or suction. Medical instrument 1322 can be deployed through elongate device 1310 and used at a target location within the anatomy. Medical instrument 1322 may include, for example, image capture probes, biopsy instruments, laser ablation fibers, and/or other surgical, diagnostic, or therapeutic tools. Medical instrument 1322 may be advanced from the distal end 1318 of the elongate device 1310 to perform the procedure and then retracted back into the channel when the procedure is complete. Medical instrument 1322 may be removed from proximal end of elongate device 1310 or from another optional instrument port (not shown) along elongate device 1310.

Elongate device 1310 may also house cables, linkages, or other steering controls (not shown) to controllably bend distal end 1318. In some examples, at least four cables are used to provide independent "up-down" steering to control a pitch of distal end 1318 and "left-right" steering to control a yaw of distal end 1318.

A position measuring device 1320 provides information about the position of instrument body 1312 as it moves on insertion stage 1308 along an insertion axis A. Position measuring device 1320 may include resolvers, encoders, potentiometers, and/or other sensors that determine the rotation and/or orientation of the actuators controlling the motion of instrument carriage 1306 and consequently the motion of instrument body 1312. In some embodiments, insertion stage 1308 is linear, while in other embodiments, the insertion stage 1308 may be curved or have a combination of curved and linear sections.

An intra-operative imaging system 1330 (e.g., imaging system 1218) is arranged near the patient P to obtain three-dimensional images of the patient while the elongate device 1310 is extended within the patient. The intra-operative imaging system 1330 may provide real-time or near real-time images of the patient P.

In some embodiments, the medical instrument 1304 or another component of a robot-assisted medical system registered to the medical instrument 1304 may include an instrument clock 1324. The imaging system 1330 may include an imaging clock 1326. The clocks 1324, 1326 may be time synchronized on a predetermined schedule or in response to a synchronization initiation event generated by a user, a control system, or a synchronization system. In some embodiments, the clocks 1324, 1326 may be components of a synchronization system that may be a centralized or distributed system further comprising servers, wired or wireless communication networks, communication devices, or other components for executing synchronization algorithms and protocols. In some embodiments, the medical instrument 1304 or another component of a robot-assisted medical system registered to the medical instrument 1304 may include a communication device 1328. The imaging system 1330 may include a communication device 1332.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

While some embodiments are provided herein with respect to medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

The methods described herein are illustrated as a set of operations or processes. Not all the illustrated processes may be performed in all embodiments of the methods. Additionally, one or more processes that are not expressly illustrated or described may be included before, after, in between, or as part of the example processes. In some embodiments, one or more of the processes may be performed by the control system (e.g., control system 112) or may be implemented, at least in part, in the form of executable code stored on non-transitory, tangible, machine-readable media that when run by one or more processors (e.g., the processors 114 of control system 112) may cause the one or more processors to perform one or more of the processes.

One or more elements in embodiments of this disclosure may be implemented in software to execute on a processor of a computer system such as control processing system. When implemented in software, the elements of the embodiments are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments are not described with reference to any particular programming language. It will be appreciated that a variety of programming languages may be used to implement the teachings as described herein.

In some instances well known methods, procedures, components, and circuits have not been described in detail so as not to unnecessarily obscure aspects of the embodiments. This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

While certain illustrative embodiments have been described and shown in the accompanying drawings, it is to be understood that such embodiments are merely illustrative of and not restrictive on the broad invention, and that the embodiments not be limited to the specific constructions and arrangements shown and described, since various other modifications may occur to those ordinarily skilled in the art.

What is claimed is:

1. A system comprising:
a processor; and
a memory having computer readable instructions stored thereon, wherein the computer readable instructions, when executed by the processor, cause the system to:
  receive, from an imaging system, image data captured during an image capture period, wherein a portion of the image data corresponds to an instrument;
  in response to receipt of a timing signal from the imaging system, record shape data for the instrument during the image capture period, the timing signal comprising a stream including the image data;
  identify a target in the image data;
  segment the portion of the image data corresponding to the instrument;
  register the image data to the shape data by comparing the shape data to the portion of the image data corresponding to the instrument; and
  update a location of the target from a pre-operative location to an intra-operative location based upon the image data.

2. The system of claim 1, wherein the shape data for the instrument is recorded from an optical fiber shape sensor extending within the instrument.

3. The system of claim 1, wherein the timing signal originates from an application programming interface of the imaging system.

4. The system of claim 1, wherein the computer readable instructions cause the system to cease recording the shape data in response to a user command.

5. The system of claim 1, wherein the computer readable instructions cause the system to automatically cease recording the shape data after the image capture period has elapsed.

6. A system, comprising:
a processor; and
a memory having computer readable instructions stored thereon, wherein the computer readable instructions, when executed by the processor, cause the system to:
  upon a determination that an instrument is parked in close proximity to a pre-operative location of a target, initiate recording of shape data for the instrument during an image capture period of an imaging system;
  receive image data from the imaging system corresponding to the image capture period, wherein a portion of the image data corresponds to the instrument;
  identify the target in the image data;

segment the portion of the image data corresponding to the instrument;

register the image data to the shape data by comparing the shape data to the portion of the image data corresponding to the instrument; and update a location of the target from the pre-operative location to an intra-operative location based upon the image data.

7. A system, comprising:

a processor; and a memory having computer readable instructions stored thereon, wherein the computer readable instructions, when executed by the processor, cause the system to:

upon a determination that a breath-hold has been initiated based upon shape data for an instrument, record the shape data during an image capture period of an imaging system;

receive image data from the imaging system corresponding to the image capture period, wherein a portion of the image data corresponds to the instrument;

identify a target in the image data;

segment the portion of the image data corresponding to the instrument;

register the image data to the shape data by comparing the shape data to the portion of the image data corresponding to the instrument; and update a location of the target from a pre-operative location to an intra-operative location based upon the image data.

8. The system of claim 1, wherein receiving the image data includes communicating with the imaging system using a DICOM standard.

9. The system of claim 1, wherein the image data is received in a maximum intensity projection ("MIP") of pseudo-CT format.

10. The system of claim 1, wherein the image data comprises at least one timestamp indicating a time at which the image data was captured.

11. The system of claim 1, wherein identifying the target is performed manually by a user selecting portions of the image data presented on a display.

12. The system of claim 1, wherein identifying the target comprises establishing a region of interest in the image data within a predetermined range of the instrument and analyzing the region of interest to segment the target from the region of interest.

13. A system comprising:

a processor; and a memory having computer readable instructions stored thereon, wherein the computer readable instructions, when executed by the processor, cause the system to:

record shape data for an instrument during an image capture period of an imaging system;

receive image data from the imaging system corresponding to the image capture period, wherein a portion of the image data corresponds to the instrument;

identify a target in the image data;

determine that identifying the target has produced unsatisfactory results;

segment the portion of the image data corresponding to the instrument;

register the image data to the shape data by comparing the shape data to the portion of the image data corresponding to the instrument; and update a location of the target from a pre-operative location to an intra-operative location based upon the image data.

14. The system of claim 13, wherein the computer readable instructions further cause the system to instruct, as a result of determining that identifying the target has produced unsatisfactory results, a user to manually identify the target in the image data.

15. A system, comprising:

a processor; and a memory having computer readable instructions stored thereon, wherein the computer readable instructions, when executed by the processor, cause the system to:

record shape data for an instrument during an image capture period of an imaging system;

receive image data from the imaging system corresponding to the image capture period, wherein a portion of the image data corresponds to the instrument;

identify a target in the image data;

segment the portion of the image data corresponding to the instrument;

determine that segmenting the portion of the image data corresponding to the instrument has produced unsatisfactory results;

register the image data to the shape data by comparing the shape data to the portion of the image data corresponding to the instrument; and update a location of the target from a pre-operative location to an intra-operative location based upon the image data.

16. The system of claim 15, wherein the computer readable instructions further cause the system to implement, as a result of determining that segmenting the portion of the image data corresponding to the instrument has produced unsatisfactory results, a low accuracy mode.

17. The system of claim 16, wherein the low accuracy mode permits registration by translation while preventing rotation.

18. The system of claim 6, wherein the determination that the instrument is parked in close proximity to the pre-operative location of the target is based at least in part on the shape data.

19. The system of claim 6, wherein the determination that the instrument is parked in close proximity to the pre-operative location of the target is based at least in part on a registration of an instrument reference frame of the shape data and a pre-operative image reference frame of an anatomical model.

20. The system of claim 7, wherein the determination that a breath-hold has been initiated is based on the shape data indicating movement of the instrument has ceased.

* * * * *